US012690863B2

(12) United States Patent

Ritz et al.

(10) Patent No.: US 12,690,863 B2

(45) Date of Patent: Jul. 28, 2026

(54) ORTHOPEDIC COMPRESSION IMPLANTS AND SYSTEMS AND METHODS OF INSTALLING THE SAME

(71) Applicant: 210 Dynamic, LLC, Castroville, TX (US)

(72) Inventors: Joseph Paul Ritz, Castroville, TX (US); Eric Alberto Marcano, San Antonio, TX (US); Andrew Salinas, Helotes, TX (US); Julian Jacob Montes, Laredo, TX (US); Damian Valdivieso, Austin, TX (US); Jason Bracco, Spring, TX (US)

(73) Assignee: 210 DYNAMIC, LLC, Castroville, TX (US)

( * ) Notice: Subject to any disclaimer, the term of this patent is extended or adjusted under 35 U.S.C. 154(b) by 0 days.

(21) Appl. No.: 19/188,913

(22) Filed: Apr. 24, 2025

(65) Prior Publication Data

US 2025/0331849 A1 Oct. 30, 2025

Related U.S. Application Data

(60) Provisional application No. 63/638,235, filed on Apr. 24, 2024.

(51) Int. Cl.
A61B 17/064 (2006.01)
A61B 17/068 (2006.01)
(Continued)

(52) U.S. Cl.
CPC ........ A61B 17/0642 (2013.01); A61B 17/151 (2013.01); A61B 17/1675 (2013.01);
(Continued)

(58) Field of Classification Search
CPC ............ A61B 17/0642; A61B 17/0682; A61B 17/151; A61B 17/1675; A61B 17/064;
(Continued)

(56) References Cited

U.S. PATENT DOCUMENTS

2010/0237128 A1 9/2010 Miller
2013/0226252 A1 8/2013 Mayer
(Continued)

OTHER PUBLICATIONS

International Search Report and Written Opinion mailed Jun. 26, 2025 for Intl Pat Appl. No. PCT/US2025/026251.

*Primary Examiner* — Marcela I. Shirsat
(74) *Attorney, Agent, or Firm* — Husch Blackwell LLP; Bryan D. Stewart

(57) ABSTRACT

Systems and methods for tibial plateau leveling osteotomy (TPLO) are disclosed. In some embodiments, a method comprises: resecting a tibial plateau to form a resected portion; arranging the resected portion in an altered position with respect to a tibial shaft; preparing a plurality of openings, the plurality of openings comprising a first opening and a third opening formed in the tibial shaft, a second opening formed in the resected portion; and advancing a staple-style orthopedic implant into the plurality of openings, the staple-style orthopedic implant comprising: a bridge having curved contour between a first end and a second end; and a plurality of legs extending from the bridge, the plurality of legs comprising: a first leg extending from the first end; a second leg extending from the second end; and a third leg, wherein each leg of the plurality of legs corresponds with each opening of the plurality of openings.

7 Claims, 11 Drawing Sheets

(51) Int. Cl.

| | |
|---|---|
| *A61B 17/072* | (2006.01) |
| *A61B 17/10* | (2006.01) |
| *A61B 17/15* | (2006.01) |
| *A61B 17/16* | (2006.01) |
| *A61B 17/17* | (2006.01) |
| *A61B 17/56* | (2006.01) |
| *A61B 17/68* | (2006.01) |
| *A61B 17/70* | (2006.01) |
| *A61B 17/80* | (2006.01) |

(52) U.S. Cl.
CPC ... *A61B 2017/0641* (2013.01); *A61B 17/0644* (2013.01); *A61B 2017/0645* (2013.01); *A61B 2017/0646* (2013.01); *A61B 17/0682* (2013.01); *A61B 17/07207* (2013.01); *A61B 2017/07228* (2013.01); *A61B 17/10* (2013.01); *A61B 17/15* (2013.01); *A61B 17/1662* (2013.01); *A61B 17/1739* (2013.01); *A61B 17/56* (2013.01); *A61B 2017/564* (2013.01); *A61B 2017/681* (2013.01); *A61B 17/7065* (2013.01); *A61B 17/809* (2013.01)

(58) Field of Classification Search
CPC . A61B 17/0644; A61B 17/068; A61B 17/076; A61B 17/08; A61B 17/083; A61B 17/07207; A61B 17/0643; A61B 17/7065; A61B 17/809; A61B 17/56; A61B 17/10; A61B 17/15; A61B 17/1662; A61B 17/1739; A61B 2017/0641; A61B 2017/0645; A61B 2017/0646; A61B 2017/564; A61B 2017/681; A61B 2017/0688; A61B 2017/07228; A61F 2/389; A61F 2/08
USPC ......... 227/175.1, 175.2, 175.3, 175.4, 176.1, 227/177.1, 178.1, 179.1, 18, 0.1, 181.1, 227/182.1, 19, 77, 79, 901, 902; 606/75, 606/53, 60, 280, 283, 300, 331, 76–79, 606/86 R, 88, 96–98, 902, 915–916
See application file for complete search history.

(56) References Cited

U.S. PATENT DOCUMENTS

| | | | |
|---|---|---|---|
| 2019/0117219 A1* | 4/2019 | Ritz ................... | A61B 17/0642 |
| 2020/0000464 A1 | 1/2020 | Gaston et al. | |
| 2021/0022730 A1* | 1/2021 | Coleman ........... | A61B 17/1739 |
| 2021/0228206 A1 | 7/2021 | Cheney et al. | |
| 2022/0008106 A1 | 1/2022 | Ellington | |
| 2023/0111234 A1 | 4/2023 | Fallin et al. | |
| 2023/0255623 A1 | 8/2023 | Ritz | |

* cited by examiner

Figure 8:
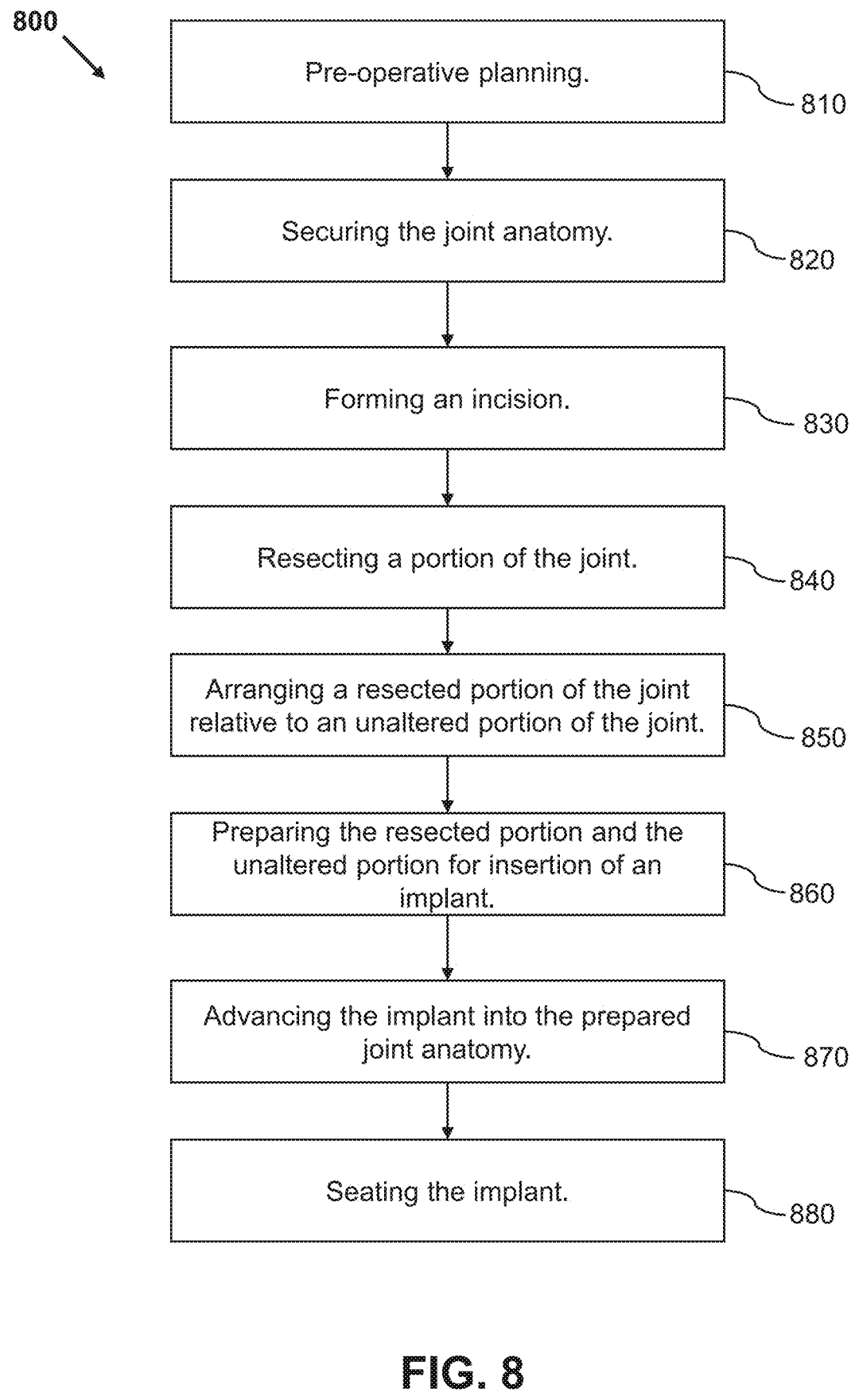

800

| Pre-operative planning. | — 810 |

| Securing the joint anatomy. | — 820 |

| Forming an incision. | — 830 |

| Resecting a portion of the joint. | — 840 |

| Arranging a resected portion of the joint relative to an unaltered portion of the joint. | — 850 |

| Preparing the resected portion and the unaltered portion for insertion of an implant. | — 860 |

| Advancing the implant into the prepared joint anatomy. | — 870 |

| Seating the implant. | — 880 |

ORTHOPEDIC COMPRESSION IMPLANTS AND SYSTEMS AND METHODS OF INSTALLING THE SAME

CROSS-REFERENCE TO RELATED APPLICATIONS

This application claims the benefit of priority to U.S. Provisional Patent Application No. 63/638,235 filed Apr. 24, 2024, which is incorporated herein by reference in its entirety.

BACKGROUND

The knee joint includes the femur, tibia, patella, and fibula bound by several ligaments such that the femur and the tibia articulate smoothly via the medial and lateral menisci when an animal moves or walks. In particular, the cranial cruciate ligament (CCL) stabilizes the knee joint, specifically to mitigate anterior translation and internal rotation of the tibia relative to the femur when the animal moves, and to provide support for weight-bearing. However, CCL injuries are a common cause of limb lameness in animals. For instance, the CCL may tear, rupture, or weaken over time and cause pain and joint instability/deterioration within the knee joint. In turn, this joint instability may cause cranial tibial thrust that worsens joint instability and causes joint deterioration (e.g., arthritis formation; injury to meniscus, osteophytes, other ligaments). Thus, to restore stability and function to the knee joint, alleviate pain, and/or prevent further joint deterioration, a tibial plateau leveling osteotomy (TPLO) procedure may be performed, wherein a user resects and rotates a portion of the tibial plateau and stabilizes it in a new position within the knee joint.

Previous forms of TPLO procedures may involve relatively bulky implant systems (e.g., plates and screws) that may chafe against soft tissues within the knee joint, or may involve other implants that address insufficient portions of the joint and may require subsequent procedures to resolve downstream issues. Thus, there is a need for improved implants for TPLO procedures that reduce foreign material within the joint space while increasing joint stabilization.

BRIEF SUMMARY OF THE DISCLOSURE

The following embodiments and aspects thereof are described and illustrated in conjunction with systems, compositions and methods that are meant to be exemplary and illustrative, not limiting in scope.

The following embodiments and aspects thereof are described and illustrated in conjunction with systems, compositions, and methods that are meant to be exemplary and illustrative, not limiting in scope.

Briefly described, aspects of the present disclosure generally relate to a method for performing tibial plateau leveling osteotomy comprising: resecting a tibial plateau to form a resected portion; arranging the resected portion in an altered position with respect to a tibial shaft; preparing a plurality of openings, the plurality of openings comprising at least: a first opening and a third opening formed in the tibial shaft; a second opening formed in the resected portion; and advancing a staple-style orthopedic implant, in a deformed configuration, into the plurality of openings, the staple-style orthopedic implant comprising: a bridge having a first end and a second end; and a plurality of legs extending from the bridge, the plurality of legs comprising at least: a first leg extending from the first end; a second leg extending from the second end; and a third leg, wherein each leg of the plurality of legs corresponds with each opening of the plurality of openings.

According to a second aspect, the method of the first aspect or any other aspect, wherein the deformed configuration comprises each leg of the plurality of legs oriented parallel to other legs of the plurality of legs.

According to a third aspect, the method of the second aspect or any other aspect, wherein the third leg extends from a portion of the bridge between the first end and the second end.

According to a fourth aspect, the method of the third aspect or any other aspect, wherein the first leg extends into the first opening, the second leg extends into the second opening, and the third leg extends into the third opening.

According to a fifth aspect, the method of the fourth aspect or any other aspect, wherein the step of preparing a plurality of openings comprises drilling the plurality of openings.

According to a sixth aspect, the method of the fourth aspect or any other aspect, wherein the step of preparing a plurality of openings comprises broaching the plurality of openings.

According to a seventh aspect, the method of the fourth aspect or any other aspect, further comprising the step of allowing the staple-style orthopedic implant to return to a reformed configuration, wherein each leg of the plurality of legs is inwardly biased.

According to an eighth aspect, the method of the seventh aspect or any other aspect, further comprising the step of inserting a second staple-style orthopedic implant, in a deformed configuration, into the resected portion and the tibial shaft.

Additionally, aspects of the present disclosure generally relate to additional methods. According to a nineth aspect, the present disclosure relates to a method for performing tibial plateau leveling osteotomy, the method comprising: resecting a tibial plateau to form a resected bone portion and an unaltered bone portion; arranging the resected bone portion in an altered position with respect to the unaltered bone portion and a tibial shaft; preparing at least three openings in the resected bone portion and the unaltered bone portion, wherein two of the at least three openings are formed in the unaltered bone portion; advancing a first staple-style orthopedic implant of at least two staple-style orthopedic implants into the at least three openings, the first staple-style orthopedic implant comprising: a bridge extending between a first end and a second end; and at least three legs extending from the bridge, wherein each leg of the at least three legs corresponds with each opening of the at least three openings; and advancing a second staple-style orthopedic implant of the at least two staple-style orthopedic implants into the resected bone portion and the unaltered bone portion.

According to a tenth aspect, the method of the nineth aspect or any other aspect, wherein the at least three legs are configured such that a first leg extends from the first end, a second leg extends from the second end, and a third leg extends from a position on the bridge between the first end and the second end.

According to an eleventh aspect, the method of the tenth aspect or any other aspect, wherein a third opening of the at least three openings is formed in the resected bone portion.

According to a twelfth aspect, the method of the eleventh aspect or any other aspect, wherein the first leg extends into the first opening, the second leg extends into the second opening, and the third leg extends into the third opening.

According to a thirteenth aspect, the method of the twelfth aspect or any other aspect, wherein the step of preparing at least three openings comprises embedding a surface of the resected bone portion and a surface of the unaltered bone portion using a surgical tool.

According to a fourteenth aspect, the method of the thirteenth aspect or any other aspect, wherein the second staple-style orthopedic implant comprises a bridge extending between a first end and a second end, and at least three legs extending from the bridge.

According to a fifteenth aspect, the method of the thirteenth aspect or any other aspect, wherein the step of advancing a second staple-style orthopedic implant involves advancing two legs of the at least three legs of the second staple-style orthopedic implant into the unaltered bone portion.

Additionally, aspects of the present disclosure generally relate to surgical kits provided for TPLO procedures. According to a sixteenth aspect, the present disclosure relates to surgical kit for performing tibial plateau leveling osteotomy, the kit comprising: a first staple-style orthopedic implant comprising: a bridge having a first end and a second end; and a plurality of legs extending from the bridge, the plurality of legs comprising at least: a first leg extending from the first end; a second leg extending from the second end; and a third leg extending from a position on the bridge between the first end and the second end; a second staple-style orthopedic implant; a retention block for maintaining the plurality of legs in a deformed configuration; a surgical tool for forming a plurality of openings in a bone portion; a depth gauge for measuring a depth of the plurality of openings; and an insertion tool for transferring the staple-style orthopedic implant, in the deformed configuration, into the plurality of openings.

According to a seventeenth aspect, the kit of the sixteenth aspect or any other aspect, wherein the first staple-style orthopedic implant is pre-loaded onto the retention block in the deformed configuration.

According to an eighteenth aspect, the kit of the sixteenth aspect or any other aspect, wherein the first staple-style orthopedic implant is loaded onto the retention block, the first staple-style orthopedic implant transitioning from a native configuration to the deformed configuration.

According to a nineteenth aspect, the kit of the sixteenth aspect or any other aspect, wherein the plurality of legs of the first staple-style orthopedic implant comprises a fourth leg extending from a second position on the bridge between the first end and the second end.

According to a twentieth aspect, the kit of the nineteenth aspect or any other aspect, wherein the plurality of legs of the first staple-style orthopedic implant comprises a fifth leg extending from a third position on the bridge between the first end and the second end.

It will be understood by those skilled in the art that one or more aspects of this disclosure can meet certain objectives, while one or more other aspects can lead to certain other objectives. Various modifications to the illustrated embodiments will be readily apparent to those skilled in the art, and the generic principles herein can be applied to other embodiments and applications without departing from embodiments of the disclosure. Other objects, features, benefits, and advantages of the present disclosure will be apparent in this summary and descriptions of the disclosed embodiments, and will be readily apparent to those skilled in the art. Such objects, features, benefits, and advantages will be apparent from the above as taken in conjunction with the accompanying figures and all reasonable inferences to be drawn therefrom.

BRIEF DESCRIPTION OF THE DRAWINGS

FIG. 8 is a flowchart of a method for performing a TPLO procedure;

DETAILED DESCRIPTION

Figure 1:
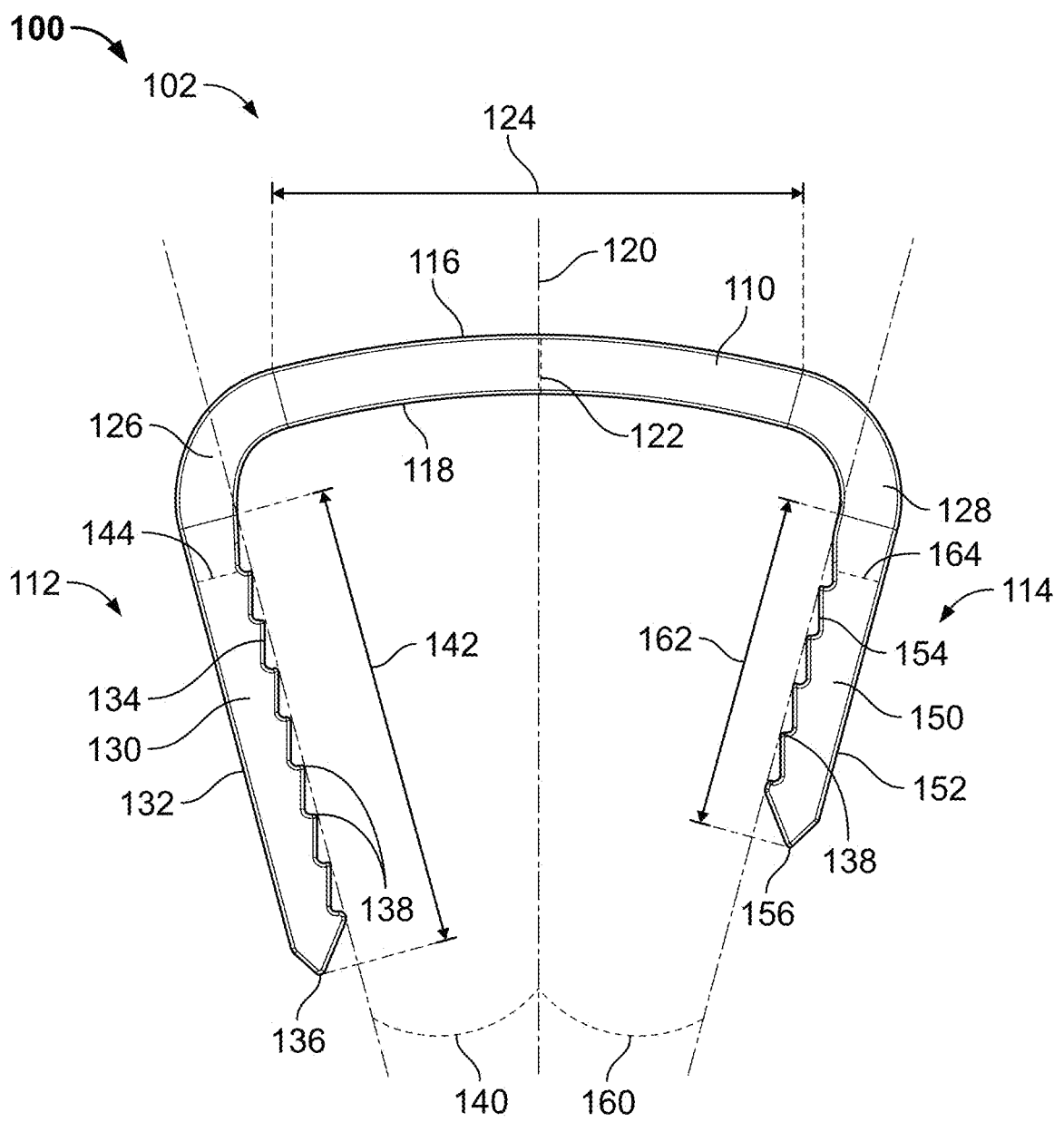
FIG. 1 shows a side view of an exemplary implant, according to one embodiment of the present disclosure.

Briefly described, aspects of the present disclosure generally relate to implants designed for the treatment of CCL injuries, as well as processes for making and using the same. In at least one embodiment, the implants discussed herein are staple-style implants, but one of ordinary skill will understand that implants contemplated herein can include other types of implants (e.g., plates and screws, combinations of plates, bridges, screws, etc.). Generally, staple-style implants are used to provide fixation and stability at a weakened bone site, and, in some embodiments, compression, based on stored strain profiles, and thus enable fusion and promote healing by limiting the distance between bone segments and through compression (e.g., Wolff's law). Specifically, the present disclosure relates to a staple-style orthopedic implant that may provide an advantageous alternative to other methods and systems for use within TPLO procedures. As will be understood, space within the knee joint may be limited, and the implants of this disclosure may be desirable to previous methods of addressing CCL injuries. For instance, the implants of the disclosure can be designed for improved performance in surgical procedures (e.g., tibial plateau leveling osteotomy) addressing CCL injuries to promote healing and restore stability to the joint.

Briefly described, aspects of the present disclosure generally relate to implants that may be inserted within a subject animal site (e.g., into one or more separated bone segments of a canine tibia) to provide compression and promote healing, as well as methods of producing and installing the same. In the case of TPLO procedures, the bone segments—which may be segments of the tibia, such as the tibial plateau—are separated and arranged in a desirable position (e.g., rotated with respect to the overall tibia) and then one or more implants may be inserted therein. In various embodiments, the present implants may be staple-style orthopedic implants similar to those disclosed in U.S. patent application Ser. No. 18/014,215, filed on Jul. 6, 2021, entitled "ORTHOPEDIC COMPRESSION IMPLANTS AND DEVICES FOR INSTALLING AND RETAINING THE SAME," which is hereby incorporated by reference in its entirety.

As described herein, the implants of the present disclosure may comprise a bridge having one or more legs extending therefrom via one or more shoulders. In some cases, the bridge may be low-profile, including a smooth, curved outer surface and/or inner surface (i.e., having a curved contour) designed to minimize interference with surrounding tissues and structures and/or reduce bulk. In other cases, the bridge may include a relatively flat outer surface and/or inner surface. In certain cases, the bridge may include a combination of curved portions and flat portions designed to match the anatomy of subject animal.

In some embodiments, the one or more legs may extend from the bridge at various angles. For instance, the one or more legs may extend from the bridge such that (1) they are initially biased inwards (i.e., native configuration), (2) they are relatively perpendicular to the bridge or parallel with respect to the other legs (i.e., deformed configuration), or (3) they are returned to an inward bias (i.e., reformed configuration). This may allow the one or more legs to provide compression, fixation, and/or stability (via stored strain) when inserted into the bone segments of the subject animal. In other embodiments, the one or more legs may exhibit a relatively straight configuration and extend relatively perpendicularly from the bridge (i.e., little to no stored strain). In certain embodiments, each leg of the one or more legs comprises features to enhance engagement with the bone segments, such as, but not limited to, a smooth outer surface, one or more teeth (or other surface modifications) extending from an inner surface, and a shaped tip.

As described herein, the implants of the present disclosure may be configured in various dimensions to accommodate different anatomical sizes, resection areas, and subject needs, such as different lengths, thicknesses, and curvatures of the bridge and legs. In certain embodiments, the implant may include at least two legs such that a first leg of the at least two legs extends from the bridge at a first shoulder and a first end, and a second leg of the at least two legs extends from the bridge at a second shoulder and a second end, wherein the first leg and the second leg are inwardly biased while the implant is in a native or reformed configuration, or relatively parallel to each other while the implant is in a deformed configuration. In some cases, the inward bias of the legs may provide improved compression, fixation, and stability when the implant is inserted into separated bone segments.

In some embodiments, the implant may include one or more additional legs (i.e., a plurality of legs), such that there may be a third, fourth, or fifth (or more) legs extending from intermediate positions along a length of the inner surface of the bridge. In such embodiments, the additional legs may allow for enhanced stability and/or distribution of compressive forces across the resected and unaltered bone segments. In some instances, implants configured with only two legs are inferior to implants configured with three or more legs because two-legged implants are more susceptible to bending, torsion, rotation, migration, and failure.

In embodiments wherein the implant comprises a multi-leg configuration, the one or more legs may be configured in any suitable orientation without departing from the principles of this disclosure. For instance, the one or more legs may be in-line with respect to each other. In other instances, the one or more legs may not be in-line with respect to each other (e.g., box-shape, y-shape, parallel, irregular, etc.). In yet other instances, in-line with respect to each other while other legs of the one or more legs may be configured in different orientations. In one non-limiting example, an implant comprising a plurality of legs may include at least two legs extending from one end, at least one leg extending from the other end, and any suitable number of legs ending from an intermediate position of the bridge such that the plurality of legs are a combination of in-line and not in-line.

In some embodiments, more than one implant may be used to stabilize the resected portion with respect to the unaltered portion. Accordingly, implants of varying dimensions and/or features may be used depending on the size of the animal, the expected activity level of the subject animal, the size of the resection, the severity of the CCL injury, etc. Additionally, the implants of the disclosure may be manufactured from any suitable materials, such as shape-memory materials (e.g., nitinol), non-shape-memory materials (e.g., titanium), or other suitable biocompatible materials which may provide improved strength, flexibility, and/or corrosion-resistance within the subject animal.

The above features (and others) will be discussed herein in the context of a staple-style orthopedic implant for use in TPLO procedures. However, it will be understood that the concepts discussed here are applicable to any suitable orthopedic implant used to support any human (or animal) anatomy without departing from the principles of this disclosure.

Referring now to the figures, FIG. 1 shows a side view of an exemplary implant 100 in a native configuration 102. In some embodiments, the implant 100 includes a bridge 110 extending between a first end 112 and a second end 114 of the implant 100, the bridge 110 comprising a smooth and curved outer (or top) surface 116 disposed opposite an inner surface 118 such that the overall implant 100 is low profile. In at least one embodiment, the low-profile contour of the outer surface 116 and inner surface 118 contributes to improved stability amidst any torsional deformation to the implant 100 resulting from insertion into prepared bone segments of a subject animal or wear and tear as the subject animal resumes ambulation, thus reducing a risk of the bridge 110 or any other portion of the implant 100 from becoming disturbed by external forces.

In some embodiments, the bridge 110 includes a length 124 such that the implant 100, from the first end 112 to the second end 114, extends across one or more bone segments within a prepared surgical site of a subject animal (e.g., knee joint). With additional reference to FIG. 11, the bridge 110 can extend from a first region on a resected portion 902A of a bone (i.e., tibia) to a second region on an unaltered portion 904 of the bone when the implant 100 is inserted within the bone segments. In some embodiments, the second region may be substantially distal from the first region. Thus, in one or more embodiments, the implants described herein overcome deficits of previous TPLO systems by compressing relatively stronger regions of the tibia (e.g., further down the tibial shaft from the resection site) to the resected and rearranged segment of tibia, thereby distributing compressive forces over a larger joint area and enhancing joint stability.

In some embodiments, the length 124 can measure at least about 10.0 mm, or about 10.0-15.0 mm, or about 15.0-20.0 mm, or about 20.0-25.0 mm, or about 25.0-30.0 mm, or about 30.0-35.0 mm, or less than about 35.0 mm. Generally, a longer bridge may include additional contouring/curvature, thereby affecting relative spacing of the legs extending from the bridge. Additionally, a longer bridge may be suitable for larger resections or larger animals, while a shorter bridge may be suitable for smaller resections or smaller animals.

In some embodiments, the outer surface 116 may have include a curvature having a constant radius, while in other embodiments, curvature to the outer surface 116 may include a variable radius. In some cases, the curvature of the outer surface 116 may be designed to match the anatomy of the subject animal to optimize functionality and integration. In one non-limiting example, a portion of the bridge 110 may be curved to contemplate an inverse geometry of the modified tibia, thus ensuring precise alignment and structural compatibility. In another non-limiting example, another portion of the bridge 110 might be curved or flat to account for regions of the unmodified tibia, thus accommodating natural anatomical variations.

In other embodiments, the outer surface 116 may have a relatively straight or flat contour. Additionally, curvature to the outer surface 116 may vary depending on the configuration of the implant 100; for instance, the outer surface 116 may include one curve or may be flat when the implant 100 is in the native configuration 102, or may include more than one curve when the implant 100 is in the deformed configuration.

In some embodiments, the bridge 110 may include a thickness 122 measuring at least about 0.5 mm, or about 0.5-1.0 mm, or about 1.0-1.5 mm, or about 1.5-2.0 mm, or about 2.0-2.5 mm, or about 2.5-3.0 mm, or about 3.0-3.5 mm, or 3.5-4.0 mm, or less than about 4.0 mm. In some embodiments, the thickness 122 may vary with the varying curvature of the bridge 110. In some embodiments, the thickness 122 may vary according to the size, age, and/or activity level of the subject animal.

According to some embodiments, the implant 100 includes one or more shoulders such that a first shoulder 126 of the one or more shoulders is positioned at the first end 112 and a second shoulder 128 of the one or more shoulders is positioned at the second end 114. In some cases, the one or more shoulders may be integrally formed with and extend from the bridge 110 while in other cases, the one or more shoulders can be assembled with the bridge 110. In other words, the one or more shoulders enable the bridge 110 to smoothly transition into one or more legs. For instance, the first shoulder 126 may allow the implant 100 to transition from the bridge 110 to a first leg 130, and the second shoulder 128 may allow the implant 100 to transition from the bridge 110 to a second leg 150. Thus, inner surfaces of the one or more shoulders can be connected with the inner surface 118 of the bridge 110, and outer surfaces of the one or more shoulders can be connected with the outer surface 116 of the bridge. Additionally, in some aspects, the one or more shoulders can exhibit a curvature having a defined radius.

In some embodiments, the first leg 130 of the one or more legs extends from the first end 112 at a first angle 140 via the first shoulder 126, and a second leg 150 of the one or more legs extends from a second end 114 at a second angle 160. In some embodiments, the one or more legs may be inwardly biased when the implant 100 is in the native configuration 102 (as shown in FIG. 1), and relatively perpendicular with respect to the bridge 110 (or parallel with respect to each other) when the implant 100 is in a deformed configuration (not shown). Additionally, in some embodiments, the first leg 130 and second leg 150 may be in-line with respect to each other, while in other embodiments, the first leg 130 and second leg 150 may be offset with respect to each other.

In various embodiments, the first leg 130 includes a length 142 measuring at least about 5.0 mm, or about 5.0-10.0 mm, or about 10.0-15.0 mm, or about 15.0-20.0 mm, or about 20.0-25.0 mm, or less than about 25.0 mm. In various embodiments, the second leg 150 includes a length 162 measuring at least about 5.0 mm, or about 5.0-10.0 mm, or about 10.0-15.0 mm, or about 15.0-20.0 mm, or about 20.0-25.0 mm, or less than about 25.0 mm. In some cases, the first leg 130 may be a different length than the second leg 150, while in other cases, the first leg 130 and the second leg 150 may be about the same length. With additional reference to FIG. 11, in some embodiments, the first leg 130 may be inserted into a first region on a resected portion 902A of the tibia (e.g., a resected portion) while the second leg 150 may be inserted into a second region on an unaltered portion 904 of the overall tibia (e.g., an unaltered portion). In other embodiments, second leg 150 may be inserted into the first region on the resected portion 902A while the first leg 130 may be inserted into the second region on the unaltered portion 904. Depending on the embodiment, the first leg 130 may be longer than the second leg 150, or the second leg 150 may be longer than the first leg 130.

In one or more embodiments, the first leg 130 includes a thickness 144 measuring at least about 0.5 mm, or about 0.5-1.0 mm, or about 1.0-2.0 mm, or about 2.0-3.0 mm, or about 3.0-4.0 mm, or about 4.0-5.0 mm, or about 5.0-6.0 mm, or less than about 6.0 mm. The second leg 150 includes a thickness 164 measuring at least about 0.5 mm, or about 0.5-1.0 mm, or about 1.0-2.0 mm, or about 2.0-3.0 mm, or about 3.0-4.0 mm, or about 4.0-5.0 mm, or about 5.0-6.0 mm, or less than about 6.0 mm. In some cases, the first leg 130 may be a different thickness than the second leg 150, while in other cases, the first leg 130 and the second leg 150 may be about the same thickness. Thus, in some embodiments, the length and/or the thickness may be different for each of the first and the second leg.

According to some embodiments, each leg of the one or more legs includes an inner surface and an outer surface and terminates in a tip. For instance, the first leg 130 can include an outer surface 132 connected with the outer surface of the first shoulder 126, and an inner surface 134 connected with the inner surface of the first shoulder 126. Additionally, the first leg 130 can terminate in a tip 136 having any suitable shape (e.g., pointed/sharp, round, square, etc.) for insertion into the first region or the second region, without departing from the principles of this disclosure. Similarly, the second leg 15 can include an outer surface 152 connected with the outer surface of the second shoulder 128, and an inner surface 154 connected with the inner surface of the second shoulder 128. The second leg 150 can terminate in a tip 156 having any suitable shape (e.g., pointed/sharp, round, square, etc.) for insertion into the first region or the second region. In some embodiments, each leg of the one or more legs may include one or more teeth 138 disposed on the respective inner surfaces 134, 154. The one or more teeth 138 may secure the implant 100 within the bone segments and prevent it from pulling out or migrating.

Although the embodiment shown with reference to FIG. 1 includes certain components and features, the principles of this disclosure may extend to implants having different or altered components, features, shapes, and/or dimensions. According to various embodiments, it will be understood that, as described herein, one or more of the implants can include any suitable combination, orientation, number, contour/curvature, positioning, and dimensions of features, such as the bridge, shoulders, legs, and teeth, among other features.

Figure 2:
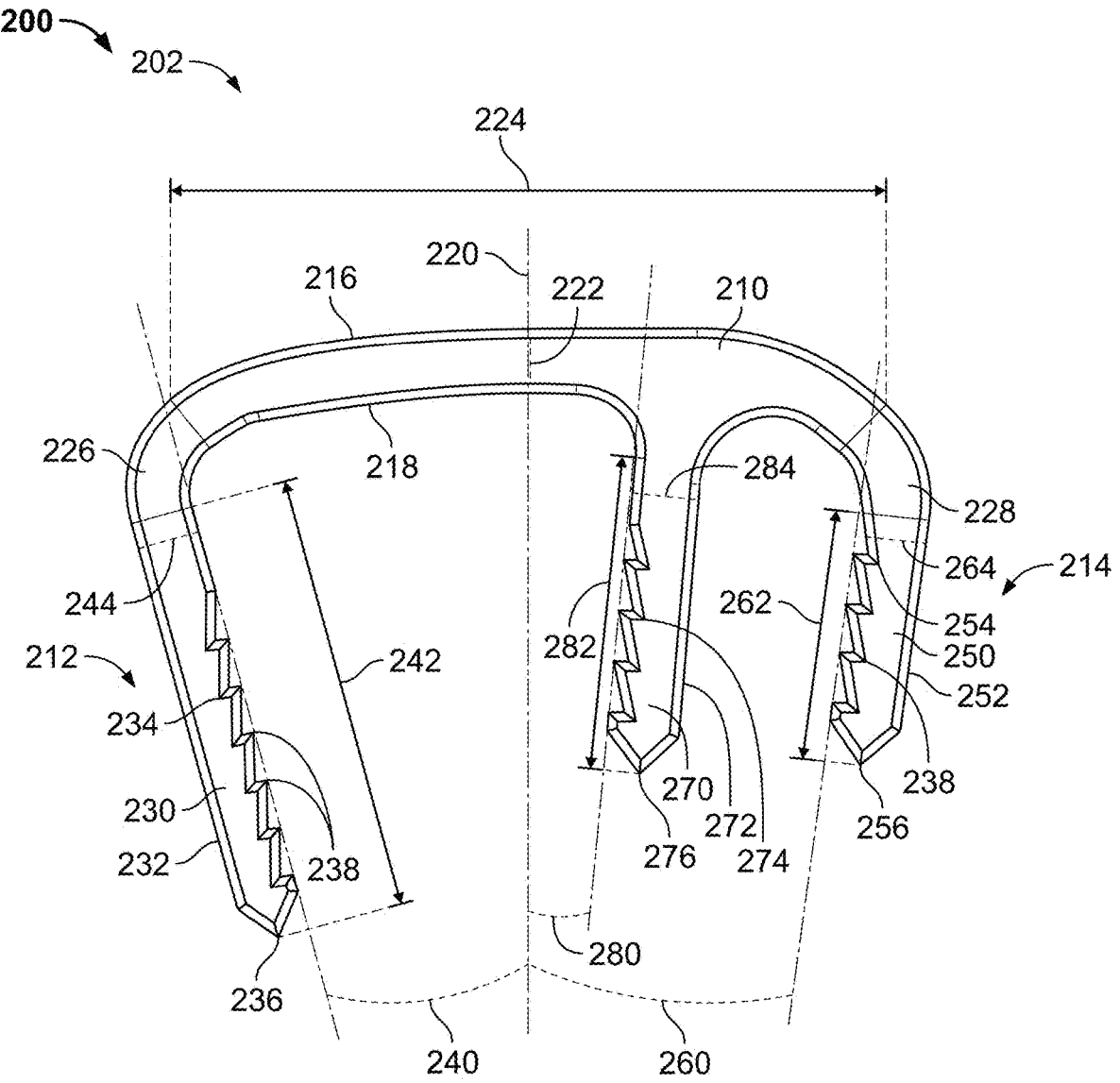
FIG. 2 shows a side view of another exemplary implant, according to one embodiment of the present disclosure.

For instance, FIG. 2 shows another exemplary implant 200. Similar to the implant 100 of FIG. 1, this embodiment depicts the implant 200 having one or more legs, or more specifically, three legs, in a native configuration 202. The implant 200 includes a bridge 210 extending between a first end 212 and a second end 214 of the implant 200, the bridge 200 comprising an outer (or top) surface 216 disposed opposite an inner surface 218 such that the overall implant 200 is low profile.

Figure 11:
FIG. 11 shows a view of the anatomy of FIG. 10 with one or more implants installed, according to one embodiment of the present disclosure.
Figure 11:
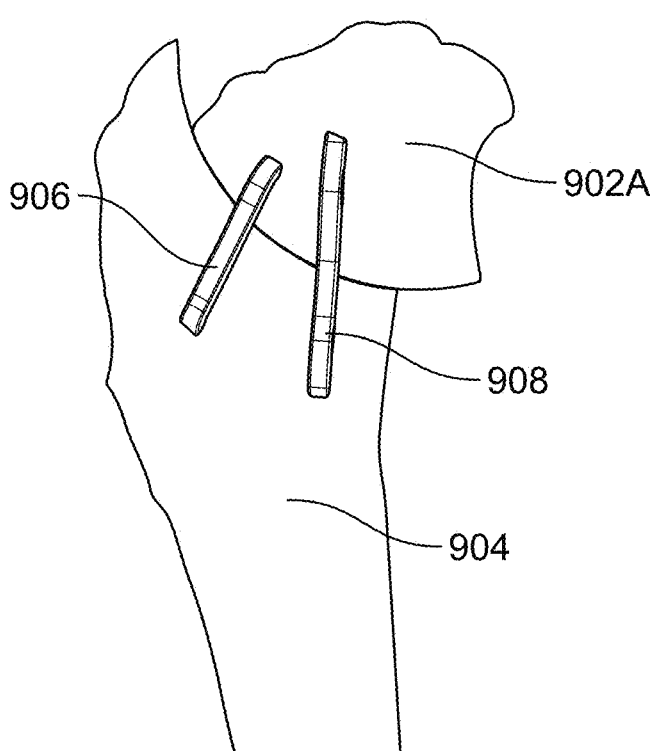

In some embodiments, the bridge 210 includes a length 224 such that the implant 200, from the first end 212 to the second end 214, extends across one or more bone segments within the prepared surgical site of a subject animal (e.g., the first region on the resected portion 902A, and the second region on the unaltered portion 904, as shown in FIG. 11). In some aspects, the length 224 can measure at least about 10.0 mm, or about 10.0-15.0 mm, or about 15.0-20.0 mm, or about 20.0-25.0 mm, or about 25.0-30.0 mm, or about 30.0-35.0 mm, or less than about 35.0 mm. Additionally, the bridge 210 includes a thickness 222 measuring at least about 0.5 mm, or about 0.5-1.0 mm, or about 1.0-1.5 mm, or about 1.5-2.0 mm, or about 2.0-2.5 mm, or about 2.5-3.0 mm, or about 3.0-3.5 mm, or 3.5-4.0 mm, or less than about 4.0 mm. In some cases, the thickness 222 may vary with the contour of the bridge 210, or according to the size, age, and/or activity level of the subject animal.

In some embodiments, the outer surface 216 may include a curvature having a constant radius, while in other embodiments, the curvature may have a variable radius. In some cases, the curvature of the outer surface 216 may be designed to match the anatomy of the subject animal. In other embodiments, the outer surface 216 may have a relatively straight or flat contour. Additionally, curvature to the outer surface 216 may vary depending on the configuration of the implant 200; for instance, the outer surface 216 may include one curve or may be flat when the implant 200 is in the native configuration 202, or may include more than one curve when the implant 200 is in the deformed configuration.

According to some embodiments, the implant 200 includes one or more shoulders such that a first shoulder 226 of the one or more shoulders is positioned at the first end 212 and a second shoulder 228 of the one or more shoulders is positioned at the second end 214. In some cases, the first shoulder 226 enables the bridge 210 to transition into a first leg 230 of the one or more legs, and the second shoulder 228 enables the bridge 210 to smoothly transition into a second leg 250 of the one or more legs. Additionally, inner surfaces of the one or more shoulders can be connected with the inner surface 218 of the bridge 210, and outer surfaces of the one or more shoulders can be connected with the outer surface 216 of the bridge. In some aspects, the one or more shoulders can exhibit a curvature having a defined radius.

In some embodiments, the implant 200 may include three legs such that the first leg 230 of the one or more legs extends from the first end 212 at a first angle 240 via the first shoulder 226, a second leg 250 of the one or more legs extends from a second end 214 at a second angle 260, and a third leg 270 extends from the inner surface 218 of the bridge 210 at a third angle 280 at a position between the first end 212 and the second end 214. In some embodiments, the position of the third leg 270 is proximal the second end 214 when compared to a center-point 220 of the bridge 210, while in other embodiments, the third leg 270 is proximal the first end 212 when compared to the center-point 220 of the bridge 210.

In some embodiments, the first leg 230 and the second leg 250 may be inwardly biased when the implant 200 is in the native configuration 202 (as shown in FIG. 2), and relatively perpendicular with respect to the bridge 210 (or parallel with respect to each other) when the implant 200 is in a deformed configuration (not shown). The third leg 270 may be biased inwardly towards one of the first leg 230 or the second leg 250 when the implant 200 is in a native configuration 202. The third leg 270 may be relatively perpendicular with respect to the bridge 210 (or parallel with respect to at least one of the first leg 230 or the second leg 250) when the implant 200 is in a deformed configuration.

In some embodiments, the first leg 230 and second leg 250 may be in-line with respect to each other, while in other embodiments, the first leg 230 and second leg 250 may be offset with respect to each other. In some embodiments, the third leg 270 may be in-line with the first leg 230 and second leg 250, while in other embodiments, the third leg 270 may extend from either of the first end 212 or second end 214, thus yielding a triangular shape to the bridge 210.

In various embodiments, the first leg 230, the second leg 250, and the third leg 270 include the following exemplary dimensions: the first leg 230 includes a length 242 measuring at least about 5.0 mm, or about 5.0-10.0 mm, or about 10.0-15.0 mm, or about 15.0-20.0 mm, or about 20.0-25.0 mm, or less than about 25.0 mm; the second leg 250 includes a length 262 measuring at least about 5.0 mm, or about 5.0-10.0 mm, or about 10.0-15.0 mm, or about 15.0-20.0 mm, or about 20.0-25.0 mm, or less than about 25.0 mm; and the third leg 270 includes a length 282 measuring at least about 5.0 mm, or about 5.0-10.0 mm, or about 10.0-15.0 mm, or about 15.0-20.0 mm, or about 20.0-25.0 mm, or less than about 25.0 mm. In some cases, the third leg 270 may be a different length than either of the first leg 230 and the second leg 250, while in other cases, the first leg 230, the second leg 250, and/or the third leg 270 may be about the same length.

For instance, the third leg 270 may be inserted into the resected segment of the tibia with the first leg 230, while the second leg 250 may be inserted into the overall tibia. Alternatively, the third leg 270 may be inserted into the overall tibia with the second leg 250, while the first leg 230 may be inserted into the resected segment. In other instances, the third leg 270 may be inserted into the resected segment of the tibia with the second leg 250, while the first leg 230 may be inserted into the overall tibia; or the third leg 270 may be inserted into the overall tibia with the first leg 230, while the second leg 250 may be inserted into the resected segment. Accordingly, the first leg 230 may be longer than the second leg 250 and/or the third leg 270. In other embodiments, the second leg 250 may be longer than the first leg 230 and/or the third leg 270. In other embodiments, any suitable combination of lengths may be contemplated as described herein.

In various embodiments, the first leg 230, the second leg 250, and the third leg 270 include the following exemplary dimensions: the first leg 230 includes a thickness 244 measuring at least about 0.5 mm, or about 0.5-1.0 mm, or about 1.0-2.0 mm, or about 2.0-3.0 mm, or about 3.0-4.0 mm, or about 4.0-5.0 mm, or about 5.0-6.0 mm, or less than about 6.0 mm; the second leg 250 includes a thickness 264 measuring at least about 0.5 mm, or about 0.5-1.0 mm, or about 1.0-2.0 mm, or about 2.0-3.0 mm, or about 3.0-4.0 mm, or about 4.0-5.0 mm, or about 5.0-6.0 mm, or less than about 6.0 mm; the third leg 270 includes a thickness 284 measuring at least about 0.5 mm, or about 0.5-1.0 mm, or about 1.0-2.0 mm, or about 2.0-3.0 mm, or about 3.0-4.0 mm, or about 4.0-5.0 mm, or about 5.0-6.0 mm, or less than about 6.0 mm. In some cases, the third leg 270 may be a different thickness than either of the first leg 230 and the second leg 250, while in other cases, the first leg 230, second leg 250, and/or the third leg 270 may be about the same thickness. In other embodiments, any suitable combination of thicknesses may be contemplated as described herein.

According to some embodiments, each leg of the one or more legs includes an inner surface and an outer surface and terminates in a tip. For instance, the first leg 230 can include an outer surface 232 connected with the outer surface of the first shoulder 226, and an inner surface 234 connected with the inner surface of the first shoulder 226. Additionally, the first leg 230 can terminate in a tip 236 having any suitable shape (e.g., pointed/sharp, round, square, etc.). Similarly, the second leg 250 can include an outer surface 252 connected with the outer surface of the second shoulder 228, and an inner surface 254 connected with the inner surface of the second shoulder 228. The second leg 250 can terminate in a tip 256 having any suitable shape. The third leg 270 can include an outer surface 272 that transitions into the inner surface 218 of the bridge 210 proximal the second end 214, and an inner surface 274 connected with the inner surface 218 of the bridge 210 proximal the first end 212. The third leg 270 can terminate in a tip 276 having any suitable shape. In some embodiments, each leg of the one or more legs may include one or more teeth 238 disposed on the respective inner surfaces 234, 254, 274.

Figure 3:
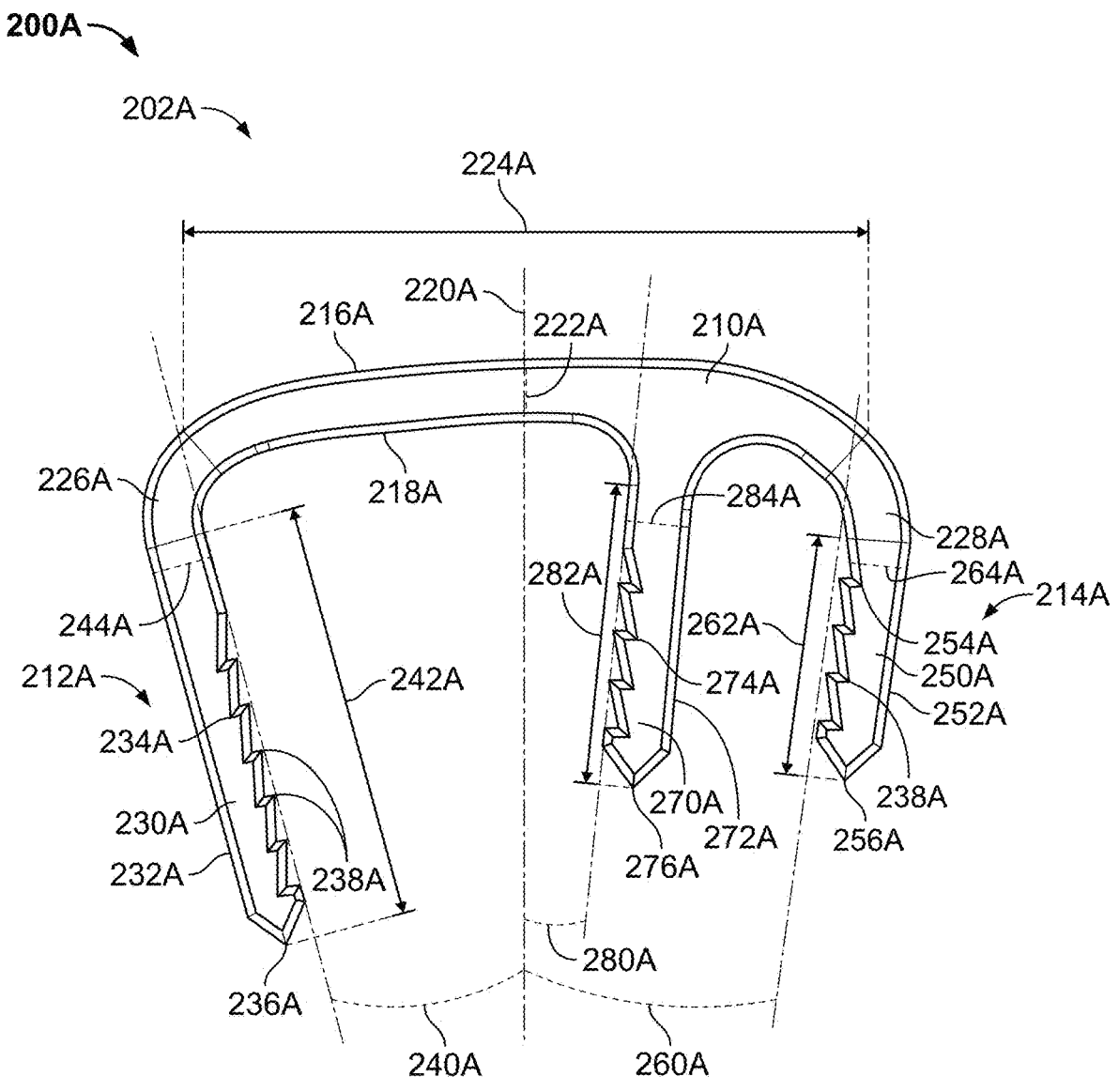
FIG. 3 shows a side view of another exemplary implant, according to one embodiment of the present disclosure.

Referring now to FIG. 3, another exemplary implant 200A is shown. Similar to the implant 200 of FIG. 2, this embodiment depicts the implant 200A having one or more legs, or more specifically, three legs, in a native configuration 202A. The implant 200A includes a bridge 210A extending between a first end 212A and a second end 214A of the implant 200A, the bridge 210A comprising an outer (or top) surface 216A disposed opposite an inner surface 218A such that the overall implant 200A is low profile. In particular, the implant 200A may be suitable for relatively small subject animals, and is sized accordingly.

In some embodiments, the bridge 210A includes a length 224A such that the implant 200A, from the first end 212A to the second end 214A, extends across one or more bone segments within the prepared surgical site of a subject animal (e.g., the first region on the resected portion 902A, and the second region on the unaltered portion 904, as shown in FIG. 11). In some aspects, the length 224A can measure at least about 5.0 mm, or about 5.0-10.0 mm, or about 10.0-15.0 mm, or about 15.0-20.0 mm, or about 20.0-25.0 mm, or about 25.0-30.0 mm, or less than about 30.0 mm. Additionally, the bridge 210A includes a thickness 222A measuring at least about 0.5 mm, or about 0.5-1.0 mm, or about 1.0-1.5 mm, or about 1.5-2.0 mm, or about 2.0-2.5 mm, or about 2.5-3.0 mm, or about 3.0-3.5 mm, or 3.5-4.0 mm, or less than about 4.0 mm. In some cases, the thickness 222A may vary with the contour of the bridge 210A, or according to the size, age, and/or activity level of the subject animal.

In some embodiments, the outer surface 216A may include a curvature having a constant radius, while in other embodiments, the curvature may have a variable radius. In some cases, the curvature of the outer surface 216A may be designed to match the anatomy of the subject animal. In other embodiments, the outer surface 216A may have a relatively straight or flat contour. Additionally, curvature to the outer surface 216A may vary depending on the configuration of the implant 200A; for instance, the outer surface 216A may include one curve or may be flat when the implant 200A is in the native configuration 202A, or may include more than one curve when the implant 200A is in the deformed configuration.

According to some embodiments, the implant 200A includes one or more shoulders such that a first shoulder 226A of the one or more shoulders is positioned at the first end 212A and a second shoulder 228A of the one or more shoulders is positioned at the second end 214A. In some cases, the first shoulder 226A enables the bridge 210A to transition into a first leg 230A of the one or more legs, and the second shoulder 228A enables the bridge 210A to smoothly transition into a second leg 250A of the one or more legs. Additionally, inner surfaces of the one or more shoulders can be connected with the inner surface 218A of the bridge 210A, and outer surfaces of the one or more shoulders can be connected with the outer surface 216A of the bridge. In some aspects, the one or more shoulders can exhibit a curvature having a defined radius.

In some embodiments, the implant 200A may include three legs such that the first leg 230A of the one or more legs extends from the first end 212A at a first angle 240A via the first shoulder 226A, a second leg 250A of the one or more legs extends from a second end 214A at a second angle 260A, and a third leg 270A extends from the inner surface 218A of the bridge 210A at a third angle 280A at a position between the first end 212A and the second end 214A. In some embodiments, the position of the third leg 270A is proximal the second end 214A when compared to a center-point 220 of the bridge 210A, while in other embodiments, the third leg 270A is proximal the first end 212A when compared to the center-point 220A of the bridge 210A.

In some embodiments, the first leg 230A and the second leg 250A may be inwardly biased when the implant 200A is in the native configuration 202A (as shown in FIG. 3), and relatively perpendicular with respect to the bridge 210A (or parallel with respect to each other) when the implant 200A is in a deformed configuration (not shown). The third leg 270A may be biased inwardly towards one of the first leg 230A or the second leg 250A when the implant 200A is in a native configuration 202A. The third leg 270A may be relatively perpendicular with respect to the bridge 210A (or parallel with respect to at least one of the first leg 230A or the second leg 250A) when the implant 200A is in a deformed configuration.

In some embodiments, the first leg 230A and second leg 250A may be in-line with respect to each other, while in other embodiments, the first leg 230A and second leg 250A may be offset with respect to each other. In some embodiments, the third leg 270A may be in-line with the first leg 230A and second leg 250A, while in other embodiments, the third leg 270A may extend from either of the first end 212A or second end 214A, thus yielding a triangular shape to the bridge 210A.

In various embodiments, the first leg 230A, the second leg 250A, and the third leg 270A include the following exemplary dimensions: the first leg 230 includes a length 242A measuring at least about 5.0 mm, or about 5.0-10.0 mm, or about 10.0-15.0 mm, or about 15.0-20.0 mm, or less than about 20.0 mm; the second leg 250A includes a length 262A measuring at least about 5.0 mm, or about 5.0-10.0 mm, or about 10.0-15.0 mm, or about 15.0-20.0 mm, or less than about 20.0 mm; the third leg 270A includes a length 282A measuring at least about 5.0 mm, or about 5.0-10.0 mm, or about 10.0-15.0 mm, or about 15.0-20.0 mm, or less than about 20.0 mm. In some cases, the third leg 270A may be a different length than either of the first leg 230A and the second leg 250A, while in other cases, the first leg 230A, the second leg 250A, and/or the third leg 270A may be about the same length.

For instance, the third leg 270A may be inserted into the resected segment of the tibia with the first leg 230A, while the second leg 250A may be inserted into the overall tibia. Alternatively, the third leg 270A may be inserted into the overall tibia with the second leg 250A, while the first leg 230A may be inserted into the resected segment. In other instances, the third leg 270A may be inserted into the resected segment of the tibia with the second leg 250A, while the first leg 230A may be inserted into the overall tibia; or the third leg 270A may be inserted into the overall tibia with the first leg 230A, while the second leg 250A may be inserted into the resected segment. Accordingly, the first leg 230A may be longer than the second leg 250A and/or the third leg 270A. In other embodiments, the second leg 250A may be longer than the first leg 230A and/or the third leg 270A. In other embodiments, any suitable combination of lengths may be contemplated as described herein.

In various embodiments, the first leg 230A, the second leg 250A, and the third leg 270A include the following exemplary dimensions: the first leg 230 includes a thickness 244A measuring at least about 0.5 mm, or about 0.5-1.0 mm, or about 1.0-2.0 mm, or about 2.0-3.0 mm, or about 3.0-4.0 mm, or about 4.0-5.0 mm, or less than about 5.0 mm; the second leg 250A includes a thickness 264A measuring at least about 0.5 mm, or about 0.5-1.0 mm, or about 1.0-2.0 mm, or about 2.0-3.0 mm, or about 3.0-4.0 mm, or about 4.0-5.0 mm, or less than about 5.0 mm; and the third leg 270A includes a thickness 284A measuring at least about 0.5 mm, or about 0.5-1.0 mm, or about 1.0-2.0 mm, or about 2.0-3.0 mm, or about 3.0-4.0 mm, or about 4.0-5.0 mm, or less than about 5.0 mm. In some cases, the third leg 270A may be a different thickness than either of the first leg 230A and the second leg 250A, while in other cases, the first leg 230A, the second leg 250A, and/or the third leg 270A may be about the same thickness. In other embodiments, any suitable combination of thicknesses may be contemplated as described herein.

According to some embodiments, each leg of the one or more legs includes an inner surface and an outer surface and terminates in a tip. For instance, the first leg 230A can include an outer surface 232A connected with the outer surface of the first shoulder 226A, and an inner surface 234A connected with the inner surface of the first shoulder 226A. Additionally, the first leg 230A can terminate in a tip 236A having any suitable shape (e.g., pointed/sharp, round, square, etc.). Similarly, the second leg 250A can include an outer surface 252A connected with the outer surface of the second shoulder 228A, and an inner surface 254A connected with the inner surface of the second shoulder 228A. The second leg 250A can terminate in a tip 256A having any suitable shape. The third leg 270A can include an outer surface 272A that transitions into the inner surface 218A of the bridge 210A proximal the second end 214A, and an inner surface 274A connected with the inner surface 218A of the bridge 210A proximal the first end 212A. The third leg 270A can terminate in a tip 276A having any suitable shape. In some embodiments, each leg of the one or more legs may include one or more teeth 238A disposed on the respective inner surfaces 234A, 254A, 274A.

Figure 4:
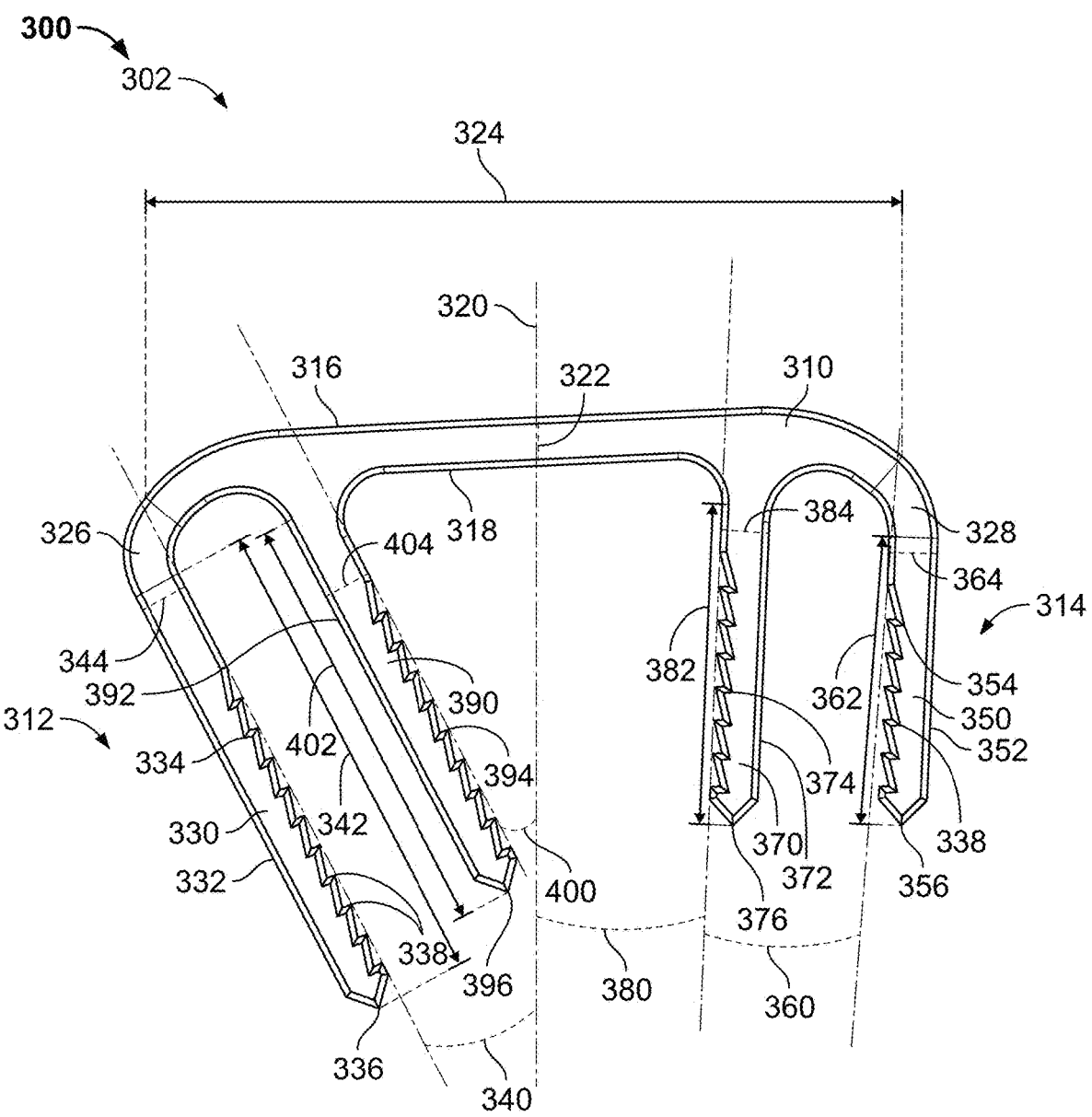
FIG. 4 shows a side view of another exemplary implant in a first configuration, according to one embodiment of the present disclosure.

Referring now to FIG. 4, another exemplary implant 300 is shown. Similar to the implant 100 of FIG. 1, this embodiment depicts the implant 300 having one or more legs, or more specifically, four legs, in a native configuration 302. The implant 300 includes a bridge 310 extending between a first end 312 and a second end 314 of the implant 300, the bridge 310 comprising an outer (or top) surface 316 disposed opposite an inner surface 318 such that the overall implant 300 is low profile.

In some embodiments, the bridge 310 includes a length 324 such that the implant 300, from the first end 312 to the second end 314, extends across one or more bone segments within the prepared surgical site of a subject animal (e.g., the first region on the resected portion 902A, and the second region on the unaltered portion 904, as shown in FIG. 11). In some aspects, the length 324 can measure at least about 10.0 mm, or about 10.0-15.0 mm, or about 15.0-20.0 mm, or about 20.0-25.0 mm, or about 25.0-30.0 mm, or about 30.0-35.0 mm, or about 35.0-40.0 mm, or less than about 40.0 mm. Additionally, the bridge 310 includes a thickness 322 measuring at least about 0.5 mm, or about 0.5-1.0 mm, or about 1.0-1.5 mm, or about 1.5-2.0 mm, or about 2.0-2.5 mm, or about 2.5-3.0 mm, or about 3.0-3.5 mm, or 3.5-4.0 mm, or less than about 4.0 mm. In some cases, the thickness 322 may vary with the contour of the bridge 310, or according to the size, age, and/or activity level of the subject animal.

In some embodiments, the outer surface 316 may include a curvature having a constant radius, while in other embodiments, the curvature may have a variable radius. In some cases, the curvature of the outer surface 316 may be designed to match the anatomy of the subject animal. In other embodiments, the outer surface 316 may have a relatively straight or flat contour. Additionally, curvature to the outer surface 316 may vary depending on the configuration of the implant 300; for instance, the outer surface 316 may include one curve or may be flat when the implant 300 is in the native configuration 302, or may include more than one curve when the implant 300 is in the deformed configuration 304 (see FIG. 5).

According to some embodiments, the implant 300 includes one or more shoulders such that a first shoulder 326 of the one or more shoulders is positioned at the first end 312 and a second shoulder 328 of the one or more shoulders is positioned at the second end 314. In some cases, the first shoulder 326 enables the bridge 310 to transition into a first leg 330 of the one or more legs, and the second shoulder 328 enables the bridge 310 to smoothly transition into a second leg 350 of the one or more legs. Additionally, inner surfaces of the one or more shoulders can be connected with the inner surface 318 of the bridge 310, and outer surfaces of the one or more shoulders can be connected with the outer surface 316 of the bridge. In some aspects, the one or more shoulders can exhibit a curvature having a defined radius.

In some embodiments, the implant 300 may include four legs such that the first leg 330 of the one or more legs extends from the first end 312 at a first angle 340 via the first shoulder 326, a second leg 350 of the one or more legs extends from a second end 314 at a second angle 360, a third leg 370 extends from the inner surface 318 of the bridge 310 at a third angle 380 at a position between the first end 312 and the second end 314, and a fourth leg 390 extends from the inner surface 318 of the bridge 310 at a fourth angle 400 at another position between the first end 312 and the second end 314. In some embodiments, the position of the third leg 370 is proximal the second end 314 when compared to a center-point 320 of the bridge 310, and the position of the fourth leg 390 is proximal the first end 312 when compared to the center-point 320. In other embodiments, the third leg 370 may be proximal the first end 312 and the fourth leg 390 may be proximal the second end 314.

Figure 5:
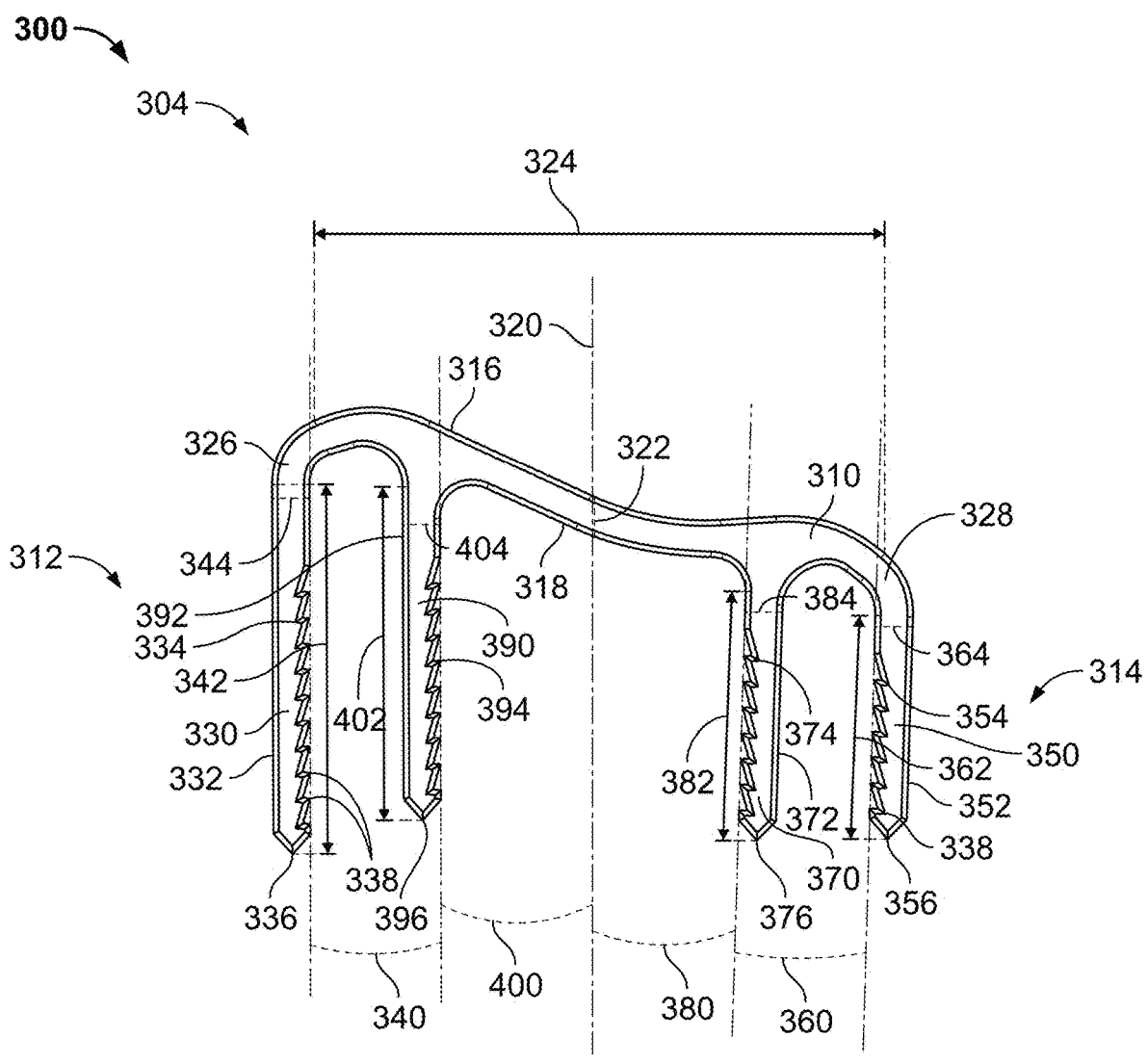
FIG. 5 shows a side view of the implant of FIG. 4 in a second configuration.

In some embodiments, the first leg 330, second leg 350, third leg 370, and fourth leg 390 may be inwardly biased when the implant 300 is in the native configuration 302 (as shown in FIG. 4). For instance, the first leg 330 and the fourth leg 390 may be biased inwardly towards the second leg 350 and the third leg 370. When the implant 300 is in a deformed configuration (as shown in FIG. 5), each of the one or more legs may be relatively perpendicular with respect to the bridge 210 (or parallel with respect to each other).

In some embodiments, the first leg 330, the second leg 350, the third leg 370, and the fourth leg 390 may be in-line with respect to each other. In other embodiments, at least one leg of the one or more legs may be offset with respect to other of the one or more legs. In certain embodiments, the third leg 370 may extend from the second end 314 while the fourth leg 390 may extend from the first end 312, thus yielding a rectangular shape to the bridge 310.

In various embodiments, the first leg 330, the second leg 350, the third leg 370, and the fourth leg 390 include the following exemplary dimensions: the first leg 330 includes a length 342 measuring at least about 5.0 mm, or about 5.0-10.0 mm, or about 10.0-15.0 mm, or about 15.0-20.0 mm, or about 20.0-25.0 mm, or less than about 25.0 mm; the second leg 350 includes a length 362 measuring at least about 5.0 mm, or about 5.0-10.0 mm, or about 10.0-15.0 mm, or about 15.0-20.0 mm, or about 20.0-25.0 mm, or less than about 25.0 mm; the third leg 370 includes a length 382 measuring at least about 5.0 mm, or about 5.0-10.0 mm, or about 10.0-15.0 mm, or about 15.0-20.0 mm, or about 20.0-25.0 mm, or less than about 25.0 mm; and the fourth leg 390 includes a length 402 measuring at least about 5.0 mm, or about 5.0-10.0 mm, or about 10.0-15.0 mm, or about 15.0-20.0 mm, or about 20.0-25.0 mm, or less than about 25.0 mm. In some cases, the fourth leg 390 may be a different length than any of the first leg 330, the second leg 350, and/or the third leg 370. In other cases, the first leg 330, the second leg 350, the third leg 370, and/or the fourth leg 390 may be about the same length.

For instance, the fourth leg 390 may be inserted into the resected segment of the tibia with the first leg 330, while the third leg 370 may be inserted into the overall tibia with second leg 350. Alternatively, the first leg 330 and fourth leg 390 may be inserted into the overall tibia, while the second leg 350 and the third leg 370 may be inserted into the resected segment. Accordingly, the first leg 330 and/or the fourth leg 390 may be longer than the second leg 350 and/or the third leg 370. In other embodiments, the second leg 350 and/or the third leg 370 may be longer than the first leg 330 and/or the fourth leg 390. In other embodiments, any suitable combination of lengths may be contemplated as described herein.

In various embodiments, the first leg 330, the second leg 350, the third leg 370, and the fourth leg 390 include the following exemplary dimensions: the first leg 330 includes a thickness 344 measuring at least about 0.5 mm, or about 0.5-1.0 mm, or about 1.0-2.0 mm, or about 2.0-3.0 mm, or about 3.0-4.0 mm, or about 4.0-5.0 mm, or about 5.0-6.0 mm, or less than about 6.0 mm; the second leg 350 includes a thickness 364 measuring at least about 0.5 mm, or about 0.5-1.0 mm, or about 1.0-2.0 mm, or about 2.0-3.0 mm, or about 3.0-4.0 mm, or about 4.0-5.0 mm, or about 5.0-6.0 mm, or less than about 6.0 mm; the third leg 370 includes a thickness 384 measuring at least about 0.5 mm, or about 0.5-1.0 mm, or about 1.0-2.0 mm, or about 2.0-3.0 mm, or about 3.0-4.0 mm, or about 4.0-5.0 mm, or about 5.0-6.0 mm, or less than about 6.0 mm; and the fourth leg 390 includes a thickness 404 measuring at least about 0.5 mm, or about 0.5-1.0 mm, or about 1.0-2.0 mm, or about 2.0-3.0 mm, or about 3.0-4.0 mm, or about 4.0-5.0 mm, or about 5.0-6.0 mm, or less than about 6.0 mm. In some cases, the fourth leg 390 may be a different thickness than any of the first leg 330, the second leg 350, and/or the third leg 370. In other cases, the first leg 330, the second leg 350, the third leg 370, and/or the fourth leg 390 may be about the same thickness. In other embodiments, any suitable combination of thicknesses may be contemplated as described herein.

According to some embodiments, each leg of the one or more legs includes an inner surface and an outer surface and terminates in a tip. For instance, the first leg 330 can include an outer surface 332 connected with the outer surface of the first shoulder 326, and an inner surface 334 connected with the inner surface of the first shoulder 326. Additionally, the first leg 330 can terminate in a tip 336 having any suitable shape (e.g., pointed/sharp, round, square, etc.). Similarly, the second leg 350 can include an outer surface 352 connected with the outer surface of the second shoulder 328, and an inner surface 354 connected with the inner surface of the second shoulder 328. The second leg 350 can terminate in a tip 356 having any suitable shape. The third leg 370 can include an outer surface 372 that transitions into the inner surface 318 of the bridge 310 proximal the second end 314, and an inner surface 374 connected with the inner surface 318 of the bridge 310 proximal the first end 312. The third leg 370 can terminate in a tip 376 having any suitable shape. The fourth leg 390 can include an outer surface 392 that transitions into the inner surface 318 of the bridge 310 proximal the first end 312, and an inner surface 394 connected with the inner surface 318 of the bridge 310 proximal the second end 314. The fourth leg 390 can terminate in a tip 396 having any suitable shape. In some embodiments, each leg of the one or more legs may include one or more teeth 338 disposed on the respective inner surfaces 334, 354, 374, 394.

Figure 6:
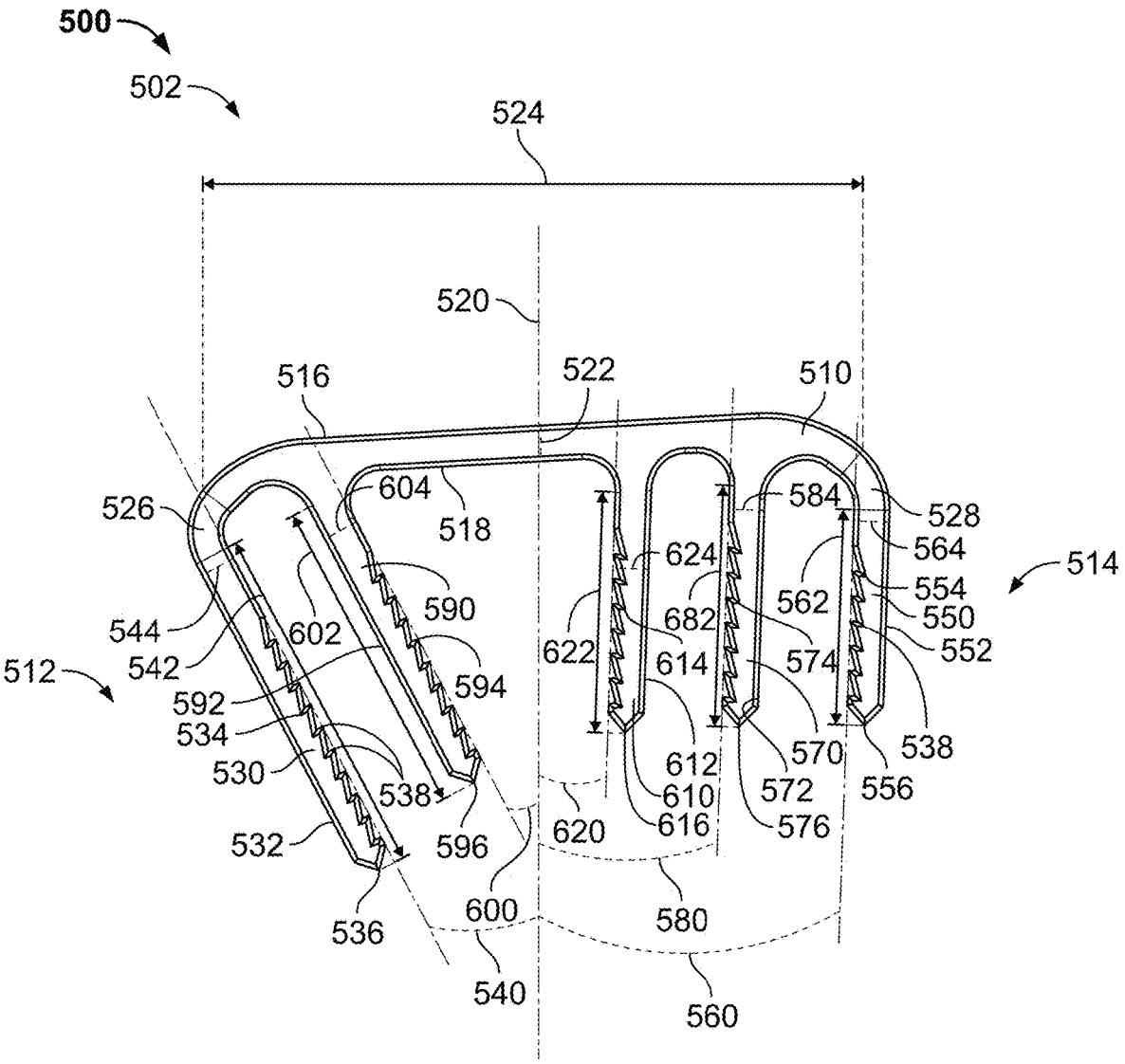
FIG. 6 shows a side view of another exemplary implant, according to one embodiment of the present disclosure.

Referring now to FIG. 6, another exemplary implant 500 is shown. Similar to the implant 100 of FIG. 1, this embodiment depicts the implant 500 having one or more legs, or more specifically, five legs, in a native configuration 502. The implant 500 includes a bridge 510 extending between a first end 512 and a second end 514 of the implant 500, the bridge 510 comprising an outer (or top) surface 516 disposed opposite an inner surface 518 such that the overall implant 500 is low profile.

In some embodiments, the bridge 510 includes a length 524 such that the implant 500, from the first end 512 to the second end 514, extends across one or more bone segments within the prepared surgical site of a subject animal (e.g., the first region on the resected portion 902A, and the second region on the unaltered portion 904, as shown in FIG. 11). In some aspects, the length 524 can measure at least about 10.0 mm, or about 10.0-15.0 mm, or about 15.0-20.0 mm, or about 20.0-25.0 mm, or about 25.0-30.0 mm, or about 30.0-35.0 mm, or about 35.0-40.0 mm, or less than about 40.0 mm. Additionally, the bridge 510 includes a thickness 522 measuring at least about 0.5 mm, or about 0.5-1.0 mm, or about 1.0-1.5 mm, or about 1.5-2.0 mm, or about 2.0-2.5 mm, or about 2.5-3.0 mm, or about 3.0-3.5 mm, or 3.5-4.0 mm, or less than about 4.0 mm. In some cases, the thickness 522 may vary with the contour of the bridge 510, or according to the size, age, and/or activity level of the subject animal.

In some embodiments, the outer surface 516 may include a curvature having a constant radius, while in other embodiments, the curvature may have a variable radius. In some cases, the curvature of the outer surface 516 may be designed to match the anatomy of the subject animal. In other embodiments, the outer surface 516 may have a relatively straight or flat contour. Additionally, curvature to the outer surface 516 may vary depending on the configuration of the implant 500; for instance, the outer surface 516 may include one curve or may be flat when the implant 500 is in the native configuration 502, or may include more than one curve when the implant 500 is in the deformed configuration (not shown).

According to some embodiments, the implant 500 includes one or more shoulders such that a first shoulder 526 of the one or more shoulders is positioned at the first end 512 and a second shoulder 528 of the one or more shoulders is positioned at the second end 514. In some cases, the first shoulder 526 enables the bridge 510 to transition into a first leg 530 of the one or more legs, and the second shoulder 528 enables the bridge 510 to smoothly transition into a second leg 550 of the one or more legs. Additionally, inner surfaces of the one or more shoulders can be connected with the inner surface 518 of the bridge 510, and outer surfaces of the one or more shoulders can be connected with the outer surface 516 of the bridge. In some aspects, the one or more shoulders can exhibit a curvature having a defined radius.

In some embodiments, the implant 500 may include five legs such that the first leg 530 of the one or more legs extends from the first end 512 at a first angle 540 via the first shoulder 526, a second leg 550 of the one or more legs extends from a second end 514 at a second angle 560, a third leg 570 extends from the inner surface 518 of the bridge 510 at a third angle 580 at a position between the first end 512 and the second end 514, a fourth leg 590 extends from the inner surface 518 of the bridge 510 at a fourth angle 600 at another position between the first end 512 and the second end 514, and a fifth leg 610 extends from the inner surface 518 of the bridge 510 at a fifth angle 620 at yet another position between the first end 512 and the second end 514. In some embodiments, the positions of the third leg 570 and the fifth leg 610 are proximal the second end 514 when compared to a center-point 520 of the bridge 510, and the position of the fourth leg 590 is proximal the first end 512 when compared to the center-point 520. In other embodiments, the third leg 570 and/or the fifth leg 610 may be proximal the first end 512 and the fourth leg 590 may be proximal the second end 514.

In some embodiments, the first leg 530, second leg 550, third leg 570, fourth leg 590, and the fifth leg 610 may be inwardly biased when the implant 500 is in the native configuration 502 (as shown in FIG. 6). For instance, the first leg 530 and the fourth leg 590 may be biased inwardly towards the second leg 550, the third leg 570, the fifth leg 610. When the implant 500 is in a deformed configuration, each of the one or more legs may be relatively perpendicular with respect to the bridge 510 (or parallel with respect to each other).

In some embodiments, the first leg 530, the second leg 550, the third leg 570, the fourth leg 590, and the fifth leg 610 may be in-line with respect to each other. In other embodiments, at least one leg of the one or more legs may be offset with respect to other of the one or more legs. In certain embodiments, the third leg 570 and/or the fifth leg 610 may extend from the second end 514 while the fourth leg 590 may extend from the first end 512, thus yielding a trapezoidal or other polygonal shape to the bridge 510.

In various embodiments, the first leg 530, the second leg 550, the third leg 570, the fourth leg 590, and the fifth leg 610 include the following exemplary dimensions: the first leg 530 includes a length 542 measuring at least about 5.0 mm, or about 5.0-10.0 mm, or about 10.0-15.0 mm, or about 15.0-20.0 mm, or about 20.0-25.0 mm, or less than about 25.0 mm; the second leg 550 includes a length 562 measuring at least about 5.0 mm, or about 5.0-10.0 mm, or about 10.0-15.0 mm, or about 15.0-20.0 mm, or about 20.0-25.0 mm, or less than about 25.0 mm; the third leg 570 includes a length 582 measuring at least about 5.0 mm, or about 5.0-10.0 mm, or about 10.0-15.0 mm, or about 15.0-20.0 mm, or about 20.0-25.0 mm, or less than about 25.0 mm; the fourth leg 590 includes a length 602 measuring at least about 5.0 mm, or about 5.0-10.0 mm, or about 10.0-15.0 mm, or about 15.0-20.0 mm, or about 20.0-25.0 mm, or less than about 25.0 mm; the fifth leg 610 includes a length 622 measuring at least about 5.0 mm, or about 5.0-10.0 mm, or about 10.0-15.0 mm, or about 15.0-20.0 mm, or about 20.0-25.0 mm, or less than about 25.0 mm. In some cases, the fifth leg 610 may be a different length than any of the first leg 530, the second leg 550, the third leg 570, and/or the fourth leg 590. In other cases, the first leg 530, the second leg 550, the third leg 570, the fourth leg 590, and/or the fifth leg 610 may be about the same length.

For instance, the fourth leg 590 may be inserted into the resected segment of the tibia with the first leg 530, while the third leg 570 and the fifth leg 610 may be inserted into the overall tibia with second leg 550. Alternatively, the first leg 530 and fourth leg 590 may be inserted into the overall tibia, while the second leg 550, the third leg 570, and the fifth leg 610 may be inserted into the resected segment. Accordingly, the first leg 530 and/or the fourth leg 590 may be longer than the second leg 550, the third leg 570, and/or the fifth leg 610. In other embodiments, the second leg 550, the third leg 570, and/or the fifth leg 610 may be longer than the first leg 530 and/or the fourth leg 590. In other embodiments, any suitable combination of lengths may be contemplated as described herein.

In various embodiments, the first leg 530, the second leg 550, the third leg 570, the fourth leg 590, and the fifth leg 610 include the following exemplary dimensions: the first leg 530 includes a thickness 544 measuring at least about 0.5 mm, or about 0.5-1.0 mm, or about 1.0-2.0 mm, or about 2.0-3.0 mm, or about 3.0-4.0 mm, or about 4.0-5.0 mm, or about 5.0-6.0 mm, or less than about 6.0 mm; the second leg 550 includes a thickness 564 measuring at least about 0.5 mm, or about 0.5-1.0 mm, or about 1.0-2.0 mm, or about 2.0-3.0 mm, or about 3.0-4.0 mm, or about 4.0-5.0 mm, or about 5.0-6.0 mm, or less than about 6.0 mm; the third leg 570 includes a thickness 584 measuring at least about 0.5 mm, or about 0.5-1.0 mm, or about 1.0-2.0 mm, or about 2.0-3.0 mm, or about 3.0-4.0 mm, or about 4.0-5.0 mm, or about 5.0-6.0 mm, or less than about 6.0 mm; the fourth leg 590 includes a thickness 604 measuring at least about 0.5 mm, or about 0.5-1.0 mm, or about 1.0-2.0 mm, or about 2.0-3.0 mm, or about 3.0-4.0 mm, or about 4.0-5.0 mm, or about 5.0-6.0 mm, or less than about 6.0 mm; the fifth leg 610 includes a thickness 624 measuring at least about 0.5 mm, or about 0.5-1.0 mm, or about 1.0-2.0 mm, or about 2.0-3.0 mm, or about 3.0-4.0 mm, or about 4.0-5.0 mm, or about 5.0-6.0 mm, or less than about 6.0 mm. In some cases, the fifth leg 610 may be a different thickness than any of the first leg 530, the second leg 550, the third leg 570, and/or the fourth leg 590. In other cases, the first leg 530, the second leg 550, the third leg 570, the fourth leg 590, and/or the fifth leg 610 may be about the same thickness. In other embodiments, any suitable combination of thicknesses may be contemplated as described herein.

According to some embodiments, each leg of the one or more legs includes an inner surface and an outer surface and terminates in a tip. For instance, the first leg 530 can include an outer surface 532 connected with the outer surface of the first shoulder 526, and an inner surface 534 connected with the inner surface of the first shoulder 526. Additionally, the first leg 530 can terminate in a tip 536 having any suitable shape (e.g., pointed/sharp, round, square, etc.). Similarly, the second leg 550 can include an outer surface 552 connected with the outer surface of the second shoulder 528, and an inner surface 554 connected with the inner surface of the second shoulder 528. The second leg 550 can terminate in a tip 556 having any suitable shape. The third leg 570 can include an outer surface 572 that transitions into the inner surface 518 of the bridge 510 proximal the second end 514, and an inner surface 574 connected with the inner surface 518 of the bridge 510 proximal the first end 512. The third leg 570 can terminate in a tip 576 having any suitable shape. The fourth leg 590 can include an outer surface 592 that transitions into the inner surface 518 of the bridge 510 proximal the first end 512, and an inner surface 594 connected with the inner surface 518 of the bridge 510 proximal the second end 514. The fourth leg 590 can terminate in a tip 596 having any suitable shape. The fifth leg 610 can include an outer surface 612 that transitions into the inner surface 518 of the bridge 510 proximal the second end 514, and an inner surface 614 connected with the inner surface 518 of the bridge 510 proximal the first end 512. The third leg 570 can terminate in a tip 576 having any suitable shape. In some embodiments, each leg of the one or more legs may include one or more teeth 538 disposed on the respective inner surfaces 334, 354, 374, 394, 614.

Figure 7:
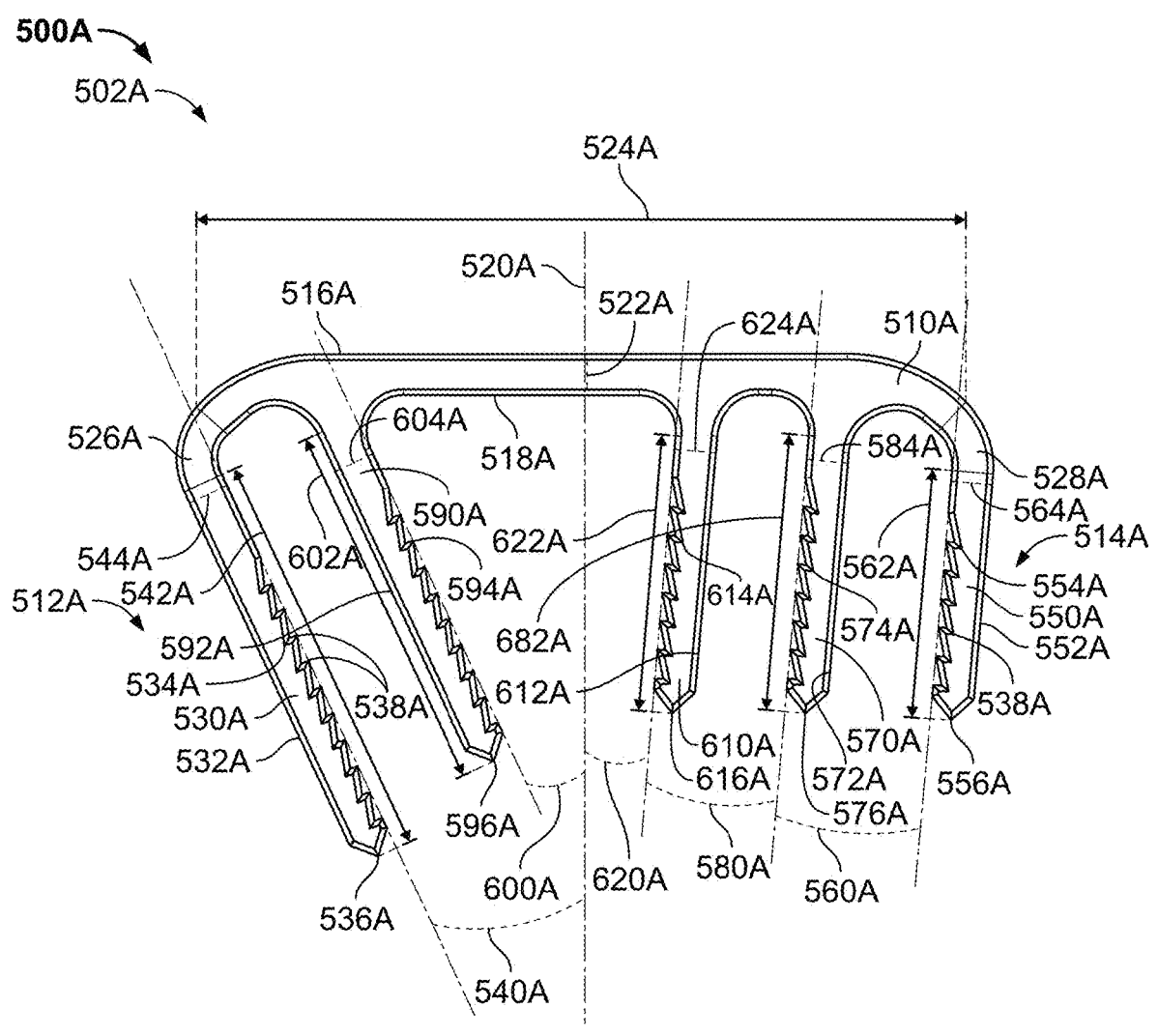
FIG. 7 shows a side view of another exemplary implant, according to one embodiment of the present disclosure.

Referring now to FIG. 7, another exemplary implant 500A is shown. Similar to the implant 500 of FIG. 6, this embodiment depicts the implant 500A having one or more legs, or more specifically, five legs, in a native configuration 502A. The implant 500A includes a bridge 510A extending between a first end 512A and a second end 514A of the implant 500A, the bridge 510A comprising an outer (or top) surface 516A disposed opposite an inner surface 518A such that the overall implant 500A is low profile. In particular, the implant 500A may be suitable for relatively large subject animals, and is sized accordingly.

In some embodiments, the bridge 510A includes a length 524A such that the implant 500A, from the first end 512A to the second end 514A, extends across one or more bone segments within the prepared surgical site of a subject animal (e.g., the first region on the resected portion 902A, and the second region on the unaltered portion 904, as shown in FIG. 11). In some aspects, the length 524A can measure at least about 10.0 mm, or about 10.0-15.0 mm, or about 15.0-20.0 mm, or about 20.0-25.0 mm, or about 25.0-30.0 mm, or about 30.0-35.0 mm, or about 35.0-40.0 mm, or about 40.0-45.0 mm, or less than about 45.0 mm. Additionally, the bridge 510A includes a thickness 522A measuring at least about 0.5 mm, or about 0.5-1.0 mm, or about 1.0-1.5 mm, or about 1.5-2.0 mm, or about 2.0-2.5 mm, or about 2.5-3.0 mm, or about 3.0-3.5 mm, or 3.5-4.0 mm, or less than about 4.0 mm. In some cases, the thickness 522A may vary with the contour of the bridge 510, or according to the size, age, and/or activity level of the subject animal.

In some embodiments, the outer surface 516A may include a curvature having a constant radius, while in other embodiments, the curvature may have a variable radius. In some cases, the curvature of the outer surface 516A may be designed to match the anatomy of the subject animal. In other embodiments, the outer surface 516A may have a relatively straight or flat contour. Additionally, curvature to the outer surface 516A may vary depending on the configuration of the implant 500A; for instance, the outer surface 516A may include one curve or may be flat when the implant 500A is in the native configuration 502A, or may include more than one curve when the implant 500A is in the deformed configuration (not shown).

According to some embodiments, the implant 500A includes one or more shoulders such that a first shoulder 526A of the one or more shoulders is positioned at the first end 512A and a second shoulder 528A of the one or more shoulders is positioned at the second end 514A. In some cases, the first shoulder 526A enables the bridge 510A to transition into a first leg 530A of the one or more legs, and the second shoulder 528A enables the bridge 510A to smoothly transition into a second leg 550A of the one or more legs. Additionally, inner surfaces of the one or more shoulders can be connected with the inner surface 518A of the bridge 510A, and outer surfaces of the one or more shoulders can be connected with the outer surface 516A of the bridge. In some aspects, the one or more shoulders can exhibit a curvature having a defined radius.

In some embodiments, the implant 500 may include five legs such that the first leg 530A of the one or more legs extends from the first end 512A at a first angle 540A via the first shoulder 526A, a second leg 550A of the one or more legs extends from a second end 514A at a second angle 560A, a third leg 570A extends from the inner surface 518A of the bridge 510A at a third angle 580A at a position between the first end 512A and the second end 514A, a fourth leg 590A extends from the inner surface 518A of the bridge 510A at a fourth angle 600A at another position between the first end 512A and the second end 514A, and a fifth leg 610A extends from the inner surface 518A of the bridge 510A at a fifth angle 620A at yet another position between the first end 512A and the second end 514A. In some embodiments, the positions of the third leg 570A and the fifth leg 610A are proximal the second end 514A when compared to a center-point 520A of the bridge 510A, and the position of the fourth leg 590A is proximal the first end 512 when compared to the center-point 520A. In other embodiments, the third leg 570A and/or the fifth leg 610A may be proximal the first end 512A and the fourth leg 590A may be proximal the second end 514A.

In some embodiments, the first leg 530A, second leg 550A, third leg 570A, fourth leg 590A, and the fifth leg 610A may be inwardly biased when the implant 500A is in the native configuration 502A (as shown in FIG. 6). For instance, the first leg 530A and the fourth leg 590A may be biased inwardly towards the second leg 550A, the third leg 570A, the fifth leg 610A. When the implant 500A is in a deformed configuration, each of the one or more legs may be relatively perpendicular with respect to the bridge 510A (or parallel with respect to each other).

In some embodiments, the first leg 530A, the second leg 550A, the third leg 570A, the fourth leg 590A, and the fifth leg 610A may be in-line with respect to each other. In other embodiments, at least one leg of the one or more legs may be offset with respect to other of the one or more legs. In certain embodiments, the third leg 570A and/or the fifth leg 610A may extend from the second end 514A while the fourth leg 590A may extend from the first end 512A, thus yielding a trapezoidal or other polygonal shape to the bridge 510A.

In various embodiments, the first leg 530A, the second leg 550A, the third leg 570A, the fourth leg 590A, and the fifth leg 610A include the following exemplary dimensions: the first leg 530A includes a length 542A measuring at least about 5.0 mm, or about 5.0-10.0 mm, or about 10.0-15.0 mm, or about 15.0-20.0 mm, or about 20.0-25.0 mm, or less than about 25.0 mm; the second leg 550A includes a length 562A measuring at least about 5.0 mm, or about 5.0-10.0 mm, or about 10.0-15.0 mm, or about 15.0-20.0 mm, or about 20.0-25.0 mm, or less than about 25.0 mm; the third leg 570A includes a length 582A measuring at least about 5.0 mm, or about 5.0-10.0 mm, or about 10.0-15.0 mm, or about 15.0-20.0 mm, or about 20.0-25.0 mm, or less than about 25.0 mm; the fourth leg 590A includes a length 602A measuring at least about 5.0 mm, or about 5.0-10.0 mm, or about 10.0-15.0 mm, or about 15.0-20.0 mm, or about 20.0-25.0 mm, or less than about 25.0 mm; and the fifth leg 610A includes a length 622A measuring at least about 5.0 mm, or about 5.0-10.0 mm, or about 10.0-15.0 mm, or about 15.0-20.0 mm, or about 20.0-25.0 mm, or less than about 25.0 mm. In some cases, the fifth leg 610A may be a different length than any of the first leg 530A, the second leg 550A, the third leg 570A, and/or the fourth leg 590A. In other cases, the first leg 530A, the second leg 550A, the third leg 570A, the fourth leg 590A, and/or the fifth leg 610A may be about the same length.

For instance, the fourth leg 590A may be inserted into the resected segment of the tibia with the first leg 530A, while the third leg 570A and the fifth leg 610A may be inserted into the overall tibia with second leg 550A. Alternatively, the first leg 530A and fourth leg 590A may be inserted into the overall tibia, while the second leg 550A, the third leg 570A, and the fifth leg 610A may be inserted into the resected segment. Accordingly, the first leg 530A and/or the fourth leg 590A may be longer than the second leg 550A, the third leg 570A, and/or the fifth leg 610A. In other embodiments, the second leg 550A, the third leg 570A, and/or the fifth leg 610A may be longer than the first leg 530A and/or the fourth leg 590A. In other embodiments, any suitable combination of lengths may be contemplated as described herein.

In various embodiments, the first leg 530A, the second leg 550A, the third leg 570A, the fourth leg 590A, and the fifth leg 610A include the following exemplary dimensions: the first leg 530A includes a thickness 544A measuring at least about 0.5 mm, or about 0.5-1.0 mm, or about 1.0-2.0 mm, or about 2.0-3.0 mm, or about 3.0-4.0 mm, or about 4.0-5.0 mm, or about 5.0-6.0 mm, or less than about 6.0 mm; the second leg 550A includes a thickness 564A measuring at least about 0.5 mm, or about 0.5-1.0 mm, or about 1.0-2.0 mm, or about 2.0-3.0 mm, or about 3.0-4.0 mm, or about 4.0-5.0 mm, or about 5.0-6.0 mm, or less than about 6.0 mm; the third leg 570A includes a thickness 584A measuring at least about 0.5 mm, or about 0.5-1.0 mm, or about 1.0-2.0 mm, or about 2.0-3.0 mm, or about 3.0-4.0 mm, or about 4.0-5.0 mm, or about 5.0-6.0 mm, or less than about 6.0 mm; the fourth leg 590A includes a thickness 604A measuring at least about 0.5 mm, or about 0.5-1.0 mm, or about 1.0-2.0 mm, or about 2.0-3.0 mm, or about 3.0-4.0 mm, or about 4.0-5.0 mm, or about 5.0-6.0 mm, or less than about 6.0 mm; and the fifth leg 610A includes a thickness 624A measuring at least about 0.5 mm, or about 0.5-1.0 mm, or about 1.0-2.0 mm, or about 2.0-3.0 mm, or about 3.0-4.0 mm, or about 4.0-5.0 mm, or about 5.0-6.0 mm, or less than about 6.0 mm. In some cases, the fifth leg 610A may be a different thickness than any of the first leg 530A, the second leg 550A, the third leg 570A, and/or the fourth leg 590A. In other cases, the first leg 530A, the second leg 550A, the third leg 570A, the fourth leg 590A, and/or the fifth leg 610A may be about the same thickness. In other embodiments, any suitable combination of thicknesses may be contemplated as described herein.

According to some embodiments, each leg of the one or more legs includes an inner surface and an outer surface and terminates in a tip. For instance, the first leg 530A can include an outer surface 532A connected with the outer surface of the first shoulder 526A, and an inner surface 534A connected with the inner surface of the first shoulder 526A. Additionally, the first leg 530A can terminate in a tip 536A having any suitable shape (e.g., pointed/sharp, round, square, etc.). Similarly, the second leg 550A can include an outer surface 552A connected with the outer surface of the second shoulder 528A, and an inner surface 554A connected with the inner surface of the second shoulder 528. The second leg 550A can terminate in a tip 556A having any suitable shape. The third leg 570A can include an outer surface 572A that transitions into the inner surface 518A of the bridge 510A proximal the second end 514A, and an inner surface 574A connected with the inner surface 518A of the bridge 510A proximal the first end 512A. The third leg 570A can terminate in a tip 576A having any suitable shape. The fourth leg 590A can include an outer surface 592A that transitions into the inner surface 518A of the bridge 510A proximal the first end 512A, and an inner surface 594A connected with the inner surface 518A of the bridge 510 proximal the second end 514A. The fourth leg 590A can terminate in a tip 596A having any suitable shape. The fifth leg 610A can include an outer surface 612A that transitions into the inner surface 518A of the bridge 510A proximal the second end 514A, and an inner surface 614A connected with the inner surface 518A of the bridge 510A proximal the first end 512A. The third leg 570A can terminate in a tip 576A having any suitable shape. In some embodiments, each leg of the one or more legs may include one or more teeth 538A disposed on the respective inner surfaces 534A, 554A, 574A, 594A, 614A.

Referring now to FIG. 8, a flowchart of an exemplary TPLO method 800 is shown, according to some embodiments. The method 800 can address CCL or other soft tissue injuries within the joint of a subject animal (i.e., knee joint), comprising the following steps: (1) pre-operative planning 810; (2) securing the joint anatomy 820; (3) forming an incision 830; (4) resecting a portion of the joint 840; (5) translating or re-arranging a resected portion of the joint relative to an unaltered portion of the joint 850; (6) preparing the resected portion and the unaltered portion for insertion of an implant 860; (7) advancing the implant into the prepared joint anatomy 870; and (8) seating the implant 880.

In some embodiments, step 810 may involve pre-operative planning to define an area for resecting a portion of the tibial plateau within the knee joint of a subject animal, including determining the size, shape, and orientation of the implant to be used. Additionally, the user may select one or more implants (e.g., implants 100, 200, 200A, 300, 500, 500A) based on this pre-operative planning to determine desirable implant size, number, and configuration. Alternatively, the user may select any number of suitable implants based on intraoperative measurements, such as using a depth gauge, sizer, or template. In alternative implementations, any suitable variations to the implants of this disclosure may be used (e.g., plates, screws, nails, etc.).

In some embodiments, step 820 may involve securing the knee joint in a desirable position using clamping instruments to stabilize the joint for the procedure.

In some embodiments, step 830 may involve forming an incision on the knee over the defined area to access the knee joint, specifically the tibial plateau.

Figure 9:
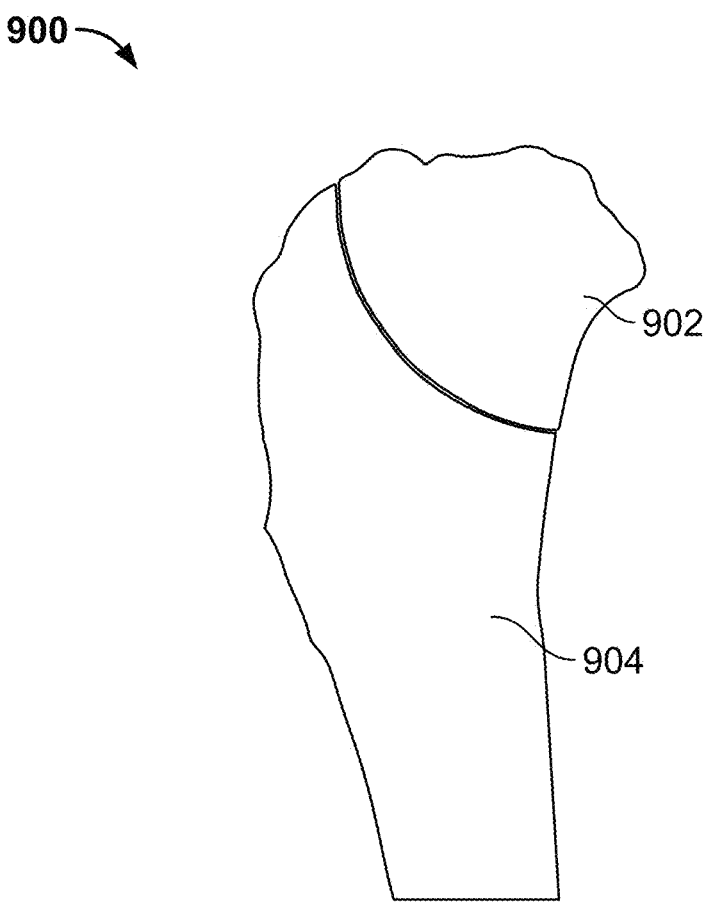
FIG. 9 shows a view of unaltered, exemplary subject anatomy.

With additional reference to FIG. 9, in some embodiments, step 840 may involve resecting one or more portions of the tibial plateau (i.e., performing an osteotomy) to create a resected portion 902 and expose an unaltered portion 904 of the tibial shaft.

Figure 10:
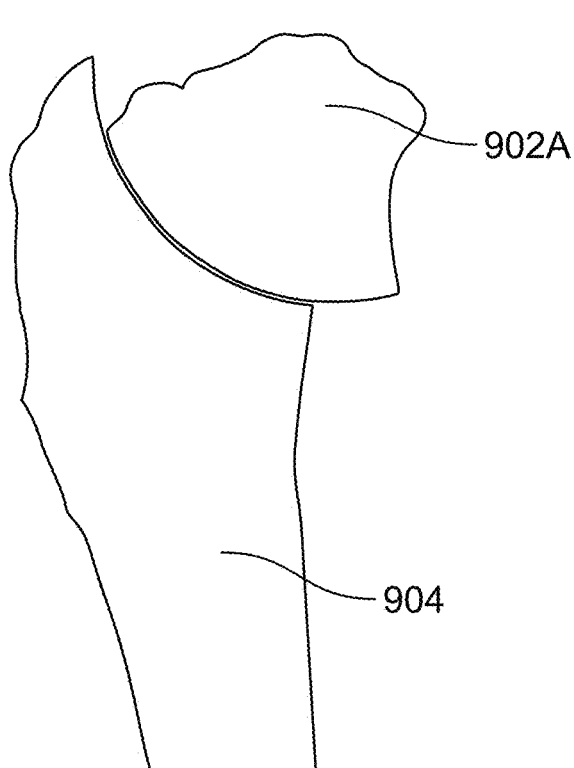
FIG. 10 shows a view of altered, exemplary subject anatomy.

With additional reference to FIG. 10, in some embodiments, step 850 may involve translating (or rotating or otherwise re-positioning) the resected portion to an altered position 902A relative to the overall tibia, or unaltered portion 904, to achieve the desired alignment or rotation of the tibial plateau. In this way, the altered resected portion 902A and the unaltered portion 904 may be opposed with respect to each other. In some cases, additional clamping instruments may be used to secure and retain the bone segments.

In some embodiments, step 860 may involve drilling one or more holes or openings (or a plurality of openings) into a surface of the altered resected portion 902A and one or more holes into a surface of the unaltered portion 904 using a drill, which may facilitate improved insertion of the one or more implants. In some cases, a plurality of holes or openings may be formed in the bone surfaces. In other embodiments, step 860 may involve impacting or otherwise embedding a surface of the altered resected portion 902A and a surface of the unaltered portion 904 using a broach guide. In this way, the user may facilitate proper implant insertion and alignment by creating paths that correspond to one or more legs of an implant. In some cases, a desirable area of the unaltered portion 904 may be a relatively distal area on the tibial shaft when compared to the line of resection. In one non-limiting example, at least two holes or openings may be formed on the surface of the tibial shaft, or unaltered portion. In another non-limiting example, at least three openings may be formed in the bone segments.

With additional reference to FIG. 11, in some embodiments, step 870 may involve advancing (or inserting) one or more implants 906, 908 into the prepared surfaces of the altered resected portion 902A and the unaltered portion 904 such that the one or more legs of the implants 906, 908 extend into the tibial plateau and a distal area of the tibial shaft. In one non-limiting example, two legs of an implant may be inserted into two holes formed on the surface of the tibial shaft. For instance, a first leg and a third leg may be inserted into a first opening and a third opening formed in the tibial shaft, while a second leg may be inserted into a second opening on the resected portion. In other instances, any suitable number of openings may be formed in the surfaces of the tibial shaft/unaltered portion and the resected portion (e.g., three, four, five) to receive any suitable number of implant legs (e.g., three, four, five). In another non-limiting example, more than one implant may be advanced into the prepared surfaces (e.g., two implants, three implants, four implants, etc.).

In some cases, step 870 may be performed manually by a user, while in other cases, it may be performed using an insertion tool. In some aspects, the one or more implants 906, 908 may be altered from a native configuration (e.g., the one or more legs are biased inwardly towards each other) to a deformed configuration (e.g., the one or more legs are relatively parallel to each other and perpendicular with respect to a bridge of the implant) via manual action by a user, the insertion tool, or a protection/retention block. In certain aspects, the one or more implants may be provided as pre-loaded onto a retention block or an inserter tool in the deformed configuration. In one non-limiting example, the one or more implants may be provided as pre-loaded onto a retention block and then transferred to an insertion tool. Thus, use of an insertion tool or retention block in this manner may shield the one or more legs and surrounding tissue (e.g., if staple is not correctly deformed) from damage prior to and during insertion.

In some embodiments, step 880 may involve seating or allowing the one or more implants 906, 908 to return to a reformed configuration once inserted into the prepared surfaces of the altered resected portion 902A and the unaltered portion 904. The reformed configuration allows the one or more legs to provide compression and/or fixation within the knee joint between the unaltered portion and the resected portion. The user may then suture the incision. In some cases, step 880 may involve disengaging an inserter tool from the implant once the implant is suitably inserted within the joint space.

In some embodiments, additional steps of method 800 may include verifying the stability of the implant and the alignment of the resected tibial plateau, as well as performing post-operative imaging to confirm proper implant placement.

According to various embodiments, the implants of the disclosure may be included as part of a kit, the kit comprising various tools and instruments for maintaining the implants or inserting/removing the implants. For instance, the kit may be provided with any suitable number of drills and drill components, broaches, resection guides, clamping instruments, insertion tools, sizers, templates, depth gauges (i.e., for measuring depth of any openings), or other surgical tools. Additionally, the implants may be provided pre-loaded onto an insertion tool or retention block, and in a deformed configuration. The implants and other components in a kit may be provided within the kit as sterilized or non-sterilized or a combination of sterilized or non-sterilized.

While various aspects have been described herein, additional aspects, features, and methodologies of the claimed system and/or processes will be readily discernible from the description herein, by those of ordinary skill in the art. Many embodiments and adaptations of the disclosure and claimed system and/or processes other than those herein described, as well as many variations, modifications, and equivalent arrangements and methodologies, will be apparent from or reasonably suggested by the disclosure and the foregoing description thereof, without departing from the substance or scope of the claims. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the claimed systems and/or processes. In addition, some steps may be carried out simultaneously, contemporaneously, or in synchronization with other steps.

The embodiments were chosen and described in order to explain the principles of the claimed systems and/or processes and their practical application so as to enable others skilled in the art to utilize the systems and/or processes and various embodiments and with various modifications as are suited to the particular use contemplated. Alternative embodiments will become apparent to those skilled in the art to which the claimed systems and/or processes pertain without departing from their spirit and scope. Accordingly, the scope of the claimed systems and/or processes is defined by the appended claims rather than the foregoing description and the exemplary embodiments described therein.

What is claimed is:

1. A method for performing tibial plateau leveling osteotomy, the method comprising:

resecting a tibial plateau to form a resected bone portion and an unaltered bone portion;

arranging the resected bone portion in an altered position with respect to the unaltered bone portion and a tibial shaft;

preparing at least three openings in the resected bone portion and the unaltered bone portion, wherein the at least three openings are formed in-line across the resected bone portion and the unaltered bone portion, and wherein two of the at least three openings are formed in the unaltered bone portion;

advancing a first staple-style orthopedic implant of at least two staple-style orthopedic implants into the at least three openings, the first staple-style orthopedic implant comprising:

a bridge extending between a first end and a second end; and at least three legs extending from the bridge, wherein each leg of the at least three legs:

corresponds with an opening of the at least three openings; and comprises one or more teeth for preventing pulling out of the corresponding opening; and advancing a second staple-style orthopedic implant of the at least two staple-style orthopedic implants into the resected bone portion and the unaltered bone portion, wherein a combination of the first staple-style orthopedic implant and the second staple-style orthopedic implant provides stability by reducing rotation and migration of the resected bone portion and the unaltered bone portion relative to the unaltered bone portion.

2. The method of claim 1, wherein the at least three legs are configured such that a first leg extends from the first end, a second leg extends from the second end, and a third leg extends from a position on the bridge between the first end and the second end.

3. The method of claim 2, wherein a third opening of the at least three openings is formed in the resected bone portion.

4. The method of claim 3, wherein the first leg extends into the first opening, the second leg extends into the second opening, and the third leg extends into the third opening.

5. The method of claim 4, wherein the step of preparing at least three openings comprises embedding a surface of the resected bone portion and a surface of the unaltered bone portion using a surgical tool.

6. The method of claim 5, wherein the second staple-style orthopedic implant comprises a bridge extending between a first end and a second end, and at least three legs extending from the bridge.

7. The method of claim 5, wherein the step of advancing a second staple-style orthopedic implant involves advancing two legs of the at least three legs of the second staple-style orthopedic implant into the unaltered bone portion.

*    *    *    *    *